United States Patent
Yamamoto et al.

(10) Patent No.: US 12,011,490 B2
(45) Date of Patent: Jun. 18, 2024

(54) DENTAL PHOTOCURABLE COMPOSITION EXCELLENT IN OPERABILITY AND STORAGE STABILITY

(71) Applicant: SHOFU INC., Kyoto (JP)

(72) Inventors: Kenzo Yamamoto, Kyoto (JP); Hideto Kasaba, Kyoto (JP); Daisuke Hara, Kyoto (JP); Shunsuke Miyata, Kyoto (JP)

(73) Assignee: SHOFU INC., Kyoto (JP)

( * ) Notice: Subject to any disclaimer, the term of this patent is extended or adjusted under 35 U.S.C. 154(b) by 0 days.

(21) Appl. No.: 17/692,568

(22) Filed: Mar. 11, 2022

(65) Prior Publication Data
US 2022/0401312 A1    Dec. 22, 2022

(30) Foreign Application Priority Data

| Mar. 12, 2021 | (JP) | 2021-040033 |
| Mar. 12, 2021 | (JP) | 2021-040037 |
| Mar. 12, 2021 | (JP) | 2021-040039 |
| Mar. 12, 2021 | (JP) | 2021-040040 |
| Sep. 14, 2021 | (JP) | 2021-149804 |
| Sep. 14, 2021 | (JP) | 2021-149805 |

(51) Int. Cl.
| A61K 6/896 | (2020.01) |
| A61C 5/00  | (2017.01) |
| A61K 6/17  | (2020.01) |
| A61K 6/62  | (2020.01) |
| A61K 6/71  | (2020.01) |
| A61K 6/76  | (2020.01) |
| A61K 6/77  | (2020.01) |

(52) U.S. Cl.
CPC .......... *A61K 6/896* (2020.01); *A61C 5/00* (2013.01); *A61K 6/17* (2020.01); *A61K 6/62* (2020.01); *A61K 6/71* (2020.01); *A61K 6/76* (2020.01); *A61K 6/77* (2020.01)

(58) Field of Classification Search
CPC ....................................................... A61K 6/79
See application file for complete search history.

(56) References Cited

U.S. PATENT DOCUMENTS

| 5,846,075 | A | 12/1998 | Suh et al. | |
| 7,084,182 | B2 * | 8/2006 | Hara | A61K 6/884 522/16 |
| 2005/0123762 | A1 | 6/2005 | Ori et al. | |
| 2007/0100020 | A1 | 5/2007 | Nakatsuka et al. | |
| 2008/0068862 | A1 | 3/2008 | Shimura | |
| 2009/0068123 | A1 | 3/2009 | Takei et al. | |
| 2010/0267856 | A1 | 10/2010 | Shinoda et al. | |
| 2010/0311858 | A1 * | 12/2010 | Holmes | A61K 6/20 522/47 |
| 2011/0288195 | A1 | 11/2011 | Kajikawa et al. | |
| 2017/0355857 | A1 | 12/2017 | Lee et al. | |
| 2018/0373145 | A1 | 12/2018 | Shiraishi | |
| 2019/0388355 | A1 | 12/2019 | Christensen et al. | |
| 2020/0069534 | A1 | 3/2020 | Furuhashi et al. | |

(Continued)

FOREIGN PATENT DOCUMENTS

| EP | 1 101 484 | 5/2001 |
| EP | 2 163 234 | 3/2010 |
| EP | 2 280 032 | 2/2011 |

(Continued)

OTHER PUBLICATIONS

Extended European Search Report issued Jun. 25, 2021 in corresponding European Patent Application No. 21162475.4.
Extended European Search Report issued Sep. 7, 2021 in corresponding European Patent Application No. 21162481.2.
Extended European Search Report issued Sep. 9, 2021 in corresponding European Patent Application No. 21162479.6.
Extended European Search Report issued Sep. 7, 2021 in corresponding European Patent Application No. 21162490.3.
Extended European Search Report issued Sep. 7, 2021 in corresponding European Patent Application No. 21162495.2.
Extended European Search Report issued Aug. 29, 2022 in corresponding European Patent Application No. 22161514.9.

(Continued)

*Primary Examiner* — Michael F Pepitone
(74) *Attorney, Agent, or Firm* — WENDEROTH, LIND & PONACK, L.L.P.

(57) ABSTRACT

[Problem]
To provide a dental photocurable composition which has sufficient mechanical property and whose rheological property is not deactivated even after long-term storage.
[Solution]
The dental photocurable composition of the present disclosure comprises (A) polymerizable monomer, (B) photosensitizer, (D) photopolymerization accelerator and (E) filler, wherein, the dental photocurable composition comprises (D1) aliphatic tertiary amine compound represented by formula (1) as the (D) photopolymerization accelerator, and the dental photocurable composition comprises (E1) hydrophobized silica fine particle having an average diameter of primary particle of 1 to 40 nm as the (E) filler.

[Chemical formula 1]

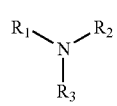

[Formula (1)]

(wherein $R_1$ represents a substituent consisting of three or more carbons having an electron-withdrawing group at α-carbon and/or β-carbon of an amine starting from N, $R_2$ represents a substituent consisting of three or more carbons which may have an electron-withdrawing group, $R_3$ represents a substituent consisting of one or more carbons which may have an electron-withdrawing group, and α-carbon of N in the formula (1) is not an electron-withdrawing group.)

13 Claims, No Drawings

(56) References Cited

U.S. PATENT DOCUMENTS

| | | | |
|---|---|---|---|
| 2021/0283022 | A1 | 9/2021 | Miyata et al. |
| 2022/0002453 | A1 | 1/2022 | Hayakawa et al. |

FOREIGN PATENT DOCUMENTS

| | | |
|---|---|---|
| EP | 2 394 628 | 12/2011 |
| EP | 3 398 975 | 11/2018 |
| EP | 3 782 598 | 2/2021 |
| JP | 2001-139843 | 5/2001 |
| JP | 2005-213231 | 8/2005 |
| JP | 2006-76973 | 3/2006 |
| JP | 2006-225350 | 8/2006 |
| JP | 4093974 | 3/2008 |
| JP | 4596786 | 10/2010 |
| JP | 4783151 | 7/2011 |
| JP | 5114498 | 10/2012 |
| JP | 5268478 | 5/2013 |
| JP | 5379563 | 10/2013 |
| JP | 5461415 | 1/2014 |
| JP | 5615720 | 9/2014 |
| JP | 2017-119803 | 7/2017 |
| JP | 2020-500879 | 1/2020 |
| WO | 99/62460 | 12/1999 |
| WO | 2006/106838 | 10/2006 |
| WO | 2008/068862 | 6/2008 |
| WO | 2018/164074 | 9/2018 |

OTHER PUBLICATIONS

Extended European Search Report issued Aug. 29, 2022 in corresponding European Patent Application No. 22161538.8.
Extended European Search Report issued Aug. 29, 2022 in corresponding European Patent Application No. 22161548.7.
Markus Griesser et al., "Photoinitiators with β-Phenylogous Cleavage: an evaluation of reaction mechanisms and performance", Macromolecules, vol. 45, pp. 1737-1745, 2012.

* cited by examiner

DENTAL PHOTOCURABLE COMPOSITION EXCELLENT IN OPERABILITY AND STORAGE STABILITY

CROSS-REFERENCE TO RELATED APPLICATIONS

This application is based on and claims the benefit of priorities from Japanese Patent Application Serial No. 2021-40033 (filed on Mar. 12, 2021), Japanese Patent Application Serial No. 2021-40037 (filed on Mar. 12, 2021), Japanese Patent Application Serial No. 2021-40039 (filed on Mar. 12, 2021), Japanese Patent Application Serial No. 2021-40040 (filed on Mar. 12, 2021), Application Serial No. 2021-149804 (filed on Sep. 14, 2021) and Application Serial No. 2021-149805 (filed on Sep. 14, 2021), the contents of which are hereby incorporated by reference in their entirety.

BACKGROUND OF THE INVENTION

Field of the Invention

The present disclosure relates to a dental photocurable composition.

Description of the Related Art

A dental photocurable composition has been used in the dental field, and applied to a dental adhesive material, a dental composite resin, a dental core build-up material, a dental resin cement, a dental coating material, a dental sealant material, a dental manicure material, a dental splinting material, a dental glass ionomer cement, a dental hard resin, a dental CAD-CAM restoration material, a dental 3D printer material and the like.

In Japanese Patent No. 5268478, a dental curable composition and a dental filling and restorative material kit containing an aliphatic tertiary amine as a photopolymerization initiator is proposed.

For imparting thixotropy, the use of a polyglycerin fatty acid ester is proposed in Japanese Patent No. 5615720, and the use of a hydrophobized silica fine particle is proposed in International Publication No. 2008/068862.

SUMMARY OF THE INVENTION

Technical Problem

However, it has been difficult in these dental photocurable compositions to satisfy all of easy adjustment of rheological property, mechanical strength suitable for dental applications and no deactivation of rheological properties even after long-term storage.

An object of the present disclosure is to provide a dental photocurable composition which has sufficient mechanical property and whose rheological property is not deactivated even after long-term storage.

Solution to Problem

A dental photocurable composition of the present disclosure comprises (A) polymerizable monomer, (B) photosensitizer, (D) photopolymerization accelerator and (E) filler, wherein, the dental photocurable composition comprises (D1) aliphatic tertiary amine compound represented by formula (1) as the (D) photopolymerization accelerator, and the dental photocurable composition comprises (E1) hydrophobized silica fine particle having an average diameter of primary particle of 1 to 40 nm as the (E) filler.

[Chemical formula 1]

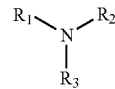

[Formula (1)]

(wherein $R_1$ represents a substituent consisting of three or more carbons having an electron-withdrawing group at α-carbon and/or ε-carbon of an amine starting from N, $R_2$ represents a substituent consisting of three or more carbons which may have an electron-withdrawing group, $R_3$ represents a substituent consisting of one or more carbons which may have an electron-withdrawing group, and α-carbon of N in the formula (1) is not an electron-withdrawing group.)

Advantageous Effects of Invention

The present disclosure may provide a dental photocurable composition which has sufficient mechanical property and whose rheological property is not deactivated even after long-term storage.

DETAILED DESCRIPTION OF THE PREFERRED EMBODIMENTS

In the present disclosure, the electron-withdrawing group in $R_1$ may be a substituent selected from a functional group selected from the group consisting of a hydroxyl group, a carboxyl group, a vinyl group, an aryl group and a halogen, and, an organic group which is bonded via an ether bond, an ester bond, a urethane bond or a urea bond and may have —OH group, —O-group, —C(O)-group, —S-group, —NH—C(O)—NH— group, —C(O)—O-group, —O—C(O)-group, —OC(O)—NH-group, —NH—C(O)—O-group, an aromatic hydrocarbon group, or a polymerizable functional group capable of radical polymerization.

In the present disclosure, the (D1) aliphatic tertiary amine compound represented by formula (1) may be an aliphatic tertiary amine compound in which $R_1$ and $R_2$ have an aliphatic substituent consisting of three or more carbons having an electron-withdrawing group at α-carbon and/or β-carbon.

In the present disclosure, the (D1) aliphatic tertiary amine compound represented by formula (1) may be an aliphatic tertiary amine compound in which $R_1$ and $R_2$ have an aryl group at α-carbon and/or β-carbon.

In the present disclosure, the (E1) hydrophobized silica fine particle having an average diameter of primary particle of 1 to 40 nm may be hydrophobized by surface treatment with dimethyl silicone oil or by surface treatment by covalent bonding of a functional group selected from trimethylsilyl group, dimethylsilyl group, methylsilyl group, alkylsilyl group having linear alkyl chain in which the carbon atom number is between 3 and 18, to the fine particle.

In the present disclosure, the dental photocurable composition may comprise 0.5 to 30 parts by mass of the (E1) hydrophobized silica fine particle having an average diameter of primary particle of 1 to 40 nm with respect to 100 mass parts of the (A) polymerizable monomer.

In the present disclosure, the dental photocurable composition may further comprise (E2) inorganic filler having an average diameter of primary particle of 0.1 to 10 μm as the (E) filler, and a total amount of the (E2) inorganic filler and the (E1) hydrophobized silica fine particle may be 100 to 400 parts by mass with respect to 100 parts by mass of the (A) polymerizable monomer.

In the present disclosure, the dental photocurable composition may further comprise an aryl iodonium salt as the (C) photoacid generator, and the aryl iodonium salt may be a salt of an anion having an organic group and one or more atoms of P, B, Al, S and Ga, and an aryl iodonium cation.

In the present disclosure, the dental photocurable composition may further comprise an aryl iodonium salt as the (C) photoacid generator, and the aryl iodonium salt may be a salt of an anion having an organic group in which at least one H is substituted with F and one or more atoms of P, B, Al, S and Ga, and an aryl iodonium cation.

In the present disclosure, the dental photocurable composition may be one pack type dental photocurable composition comprising, with respect to 100 parts by mass of the (A) polymerizable monomer,
0.02 to 1 parts by mass of the (B) photosensitizer,
0.1 to 10 parts by mass of the (D1) aliphatic tertiary amine compound,
0.5 to 30 parts by mass of the (E1) hydrophobized silica fine particle having an average diameter of primary particle of 1 to 40 nm.

In the present disclosure, the dental photocurable composition may be one pack type dental photocurable composition comprising, with respect to 100 parts by mass of the (A) polymerizable monomer,
0.02 to 1 parts by mass of the (B) photosensitizer,
0.1 to 10 parts by mass of the (C) photoacid generator,
0.1 to 10 parts by mass of the (D1) aliphatic tertiary amine compound,
0.5 to 30 parts by mass of the (E1) hydrophobized silica fine particle having an average diameter of primary particle of 1 to 40 nm.

In the present disclosure, the dental photocurable composition may be two packs type dental photocurable composition consisting of a first paste and a second paste, a mass ratio of the first paste and the second paste is 1:0.8 to 1.2,
both the first paste and the second paste comprise the (E1) hydrophobized silica fine particle having an average diameter of primary particle of 1 to 40 nm,
the dental photocurable composition comprises, with respect to 200 parts by mass of total of the (A) polymerizable monomer contained in the first paste and the second paste,
0.04 to 2 parts by mass of the (B) photosensitizer,
0.2 to 20 parts by mass of the (D1) aliphatic tertiary amine compound,
1 to 60 parts by mass of the (E1) hydrophobized silica fine particle having an average diameter of primary particle of 1 to 40 nm.

In the present disclosure, the dental photocurable composition may be two packs type dental photocurable composition consisting of a first paste and a second paste, a mass ratio of the first paste and the second paste is 1:0.8 to 1.2,
both the first paste and the second paste comprise the (E1) hydrophobized silica fine particle having an average diameter of primary particle of 1 to 40 nm,
the dental photocurable composition comprises, with respect to 200 parts by mass of total of the (A) polymerizable monomer contained in the first paste and the second paste,
0.04 to 2 parts by mass of the (B) photosensitizer,
0.2 to 20 parts by mass of the (C) photoacid generator,
0.2 to 20 parts by mass of the (D1) aliphatic tertiary amine compound,
1 to 60 parts by mass of the (E1) hydrophobized silica fine particle having an average diameter of primary particle of 1 to 40 nm.

In the present disclosure, the difference between a flowability of the dental photocurable composition after standing in a thermostatic chamber set at 50° C. for one month after preparation and a flowability of the dental photocurable composition after preparation may be 3.0 mm or less.

In the present disclosure, both the flowability of the dental photocurable composition after standing in a thermostatic chamber set at 50° C. for one month after preparation and the flowability of the dental photocurable composition after preparation may be 3.0 mm or less.

Hereinafter, each component in the dental photocurable composition of the present disclosure is described in detail. The dental photocurable composition of the present disclosure is applied as a dental adhesive material, a dental composite resin, a dental core build-up material, a dental resin cement, a dental coating material, a dental sealant material, a dental manicure material, a dental splinting material, a dental glass ionomer cement, a dental hard resin, a dental CAD-CAM restoration material, a dental 3D printer material and the like.

In a dental practice, in order to restore aesthetically and functionally a lost portion of a tooth by caries, breakages and the like, a direct method which performs restoration with a dental adhesive material and a composite resin and an indirect method which restores a prosthetic device consisting of ceramics or a dental hard resin with a dental resin cement have been performed as treatment. In addition, a dental adhesive material for adhering a dental composite resin and various dental materials and a natural tooth, a dental splinting material for fixing a mobile tooth, a dental coating material for protecting a vital tooth after forming, against a hyperesthesia, an external stimulation and secondary caries, a dental sealant material for preventing caries by filling deep grooves of a molar tooth, a dental manicure material for temporary recovering aesthetic property by masking discoloration of a tooth, and a dental core build-up material for forming an abutment tooth in the case of collapsing of a dental crown due to caries have been used. In recent years, new composite materials such as a dental CAD-CAM restoration material for preparing a prosthetic device by CAD/CAM processing and a dental 3D printer material for preparing a prosthetic device by 3D printer have been developed, and various dental materials have been used for treatment. The above-described materials are prepared into a uniform paste by mixing a resin matrix consisting of several kinds of polymerizable monomers, a filler such as an inorganic filler and an organic-inorganic composite filler, and a polymerization initiator, according to the application. As one example of some materials, a dental composite resin for filling is used by filling into a tooth in the form of uncured paste, imparting anatomical form of a natural tooth with a dental instrument such as an instrument, and curing by irradiating light with a light irradiator or the like. For the irradiation light from a light irradiator, a light source having an output of about 100 to 2000 mW/cm$^2$ in a wavelength range of about 360 to 500 nm is generally used. On the other hand, a dental resin cement is used for adhering a prosthetic device to a tooth cavity or an abutment tooth, and is cured by light irradiation after attaching the prosthetic device to the tooth cavity or the abutment tooth.

As the photopolymerization initiator used for such dental materials, a photosensitizer and a system in which a photosensitizer is combined with an appropriate photopolymerization accelerator has been widely used. As the photosensitizer, acylphosphine oxide compounds and α-diketone compounds are known, and in particular, α-diketone compounds have an ability to initiate polymerization in the wavelength range of visible light which has little effect on the human body. Furthermore, a photoacid generator and a tertiary amine compound are well known as a compound to be combined with a photosensitizer. A combination of an α-diketone compound, a photoacid generator and a tertiary amine compound has high polymerization activity with respect to irradiation light, and thus has been used in a dental material field. The dental photocurable composition containing this photopolymerization initiator exhibits excellent mechanical properties such as hardness, flexural strength and compressive strength required for various materials.

In the case of combining with an aromatic tertiary amine compound represented by ethyl 4-(dimethylamino) benzoate, α-diketone compound used as a photopolymerization initiator can exhibit good polymerization performance. However, there is a case that an aromatic tertiary amine compound causes discoloration, deterioration in sensitivity to light, and the like. Therefore, an aliphatic tertiary amine compound has been used in dental material to reduce the amount of an aromatic tertiary amine compound or replace.

On the other hand, a dental material needs to fit to various shapes according to the complex shape of a natural tooth. In order to operate the shape of the dental material as desired by the user, there is a case that the dental material contains a rheology modifier. There are two types of rheology modifiers including an organic type and an inorganic type. As the organic type, polyglycerin and the like are known, and as the inorganic type, a silica fine particle is known. Among these, it is expected to exhibit effects such as an improvement of strength and suppression of sedimentation of other filler by compounding a silica fine particle to a dental material in addition to an effect of imparting thixotropic property among rheological property.

However, when conventionally used aliphatic tertiary amine compounds such as dimethylaminoethyl methacrylate and triethanolamine coexists in a dental photocurable composition containing silica fine particle, there is a case that the rheological property is deactivated. The detailed principle is unknown, however, it is considered that although the rheological property from the silica fine particle is exhibited by moderate agglomeration due to interaction between silica fine particles in the composition, and dispersion and reaggregation due to external stress, the aggregate structure collapses due to the interaction between the silica fine particle and an aliphatic tertiary amine compound to deactivate the rheological property.

In order to solve the above problems, it has been found to using an aliphatic tertiary amine compound with a specific structure in the dental photocurable composition of the present disclosure. More specifically, it has been found that even a dental photocurable composition containing hydrophobized silica fine particle can exhibit sufficient physical property for a dental application without losing its rheological property after long-term storage by using an aliphatic tertiary amine compound which has greater steric hindrance than conventionally used aliphatic tertiary amine compound and has reduced electron density by having an electron-withdrawing group, to have completed the present disclosure.

[(A) Polymerizable Monomer]

As the (A) polymerizable monomer contained in the dental photocurable composition of the present disclosure, any polymerizable monomers can be used without limitation as long as it is known. In the polymerizable monomer or the compound having a polymerizable group described in the present disclosure, the polymerizable group preferably exhibits radical polymerizability, and specifically, from the viewpoint of easy radical polymerization, the polymerizable group is preferably (meth) acrylic group and/or (meth) acrylamide group. In the present specification, "(meth) acrylic" means acrylic and/or methacrylic, "(meth) acryloyl" means acryloyl and/or methacryloyl, "(meth) acrylate" means acrylate and/or methacrylate, and, "(meth) acrylamide" means acrylamide and/or methacrylamide. A polymerizable monomer having a substituent at the α-position of an acrylic group and/or an acrylamide group can also be preferably used. Specific examples include one having one radical polymerizable group, one having two radical polymerizable groups, one having three or more radical polymerizable groups, one having an acidic group, one having an alkoxysilyl group, and one having a sulfur atom.

Specific examples of a polymerizable monomer having one radical polymerizable group and not containing acidic group include 2-hydroxyethyl (meth) acrylate, 3-hydroxypropyl (meth) acrylate, 4-hydroxybutyl (meth) acrylate, 2-hydroxypropyl (meth) acrylate, 2-hydroxybutyl (meth) acrylate, 6-hydroxyhexyl (meth) acrylate, 10-hydroxydecyl (meth) acrylate, propylene glycol mono (meth) acrylate, glycerol mono (meth) acrylate, erythritol mono (meth) acrylate, N-methylol (meth) acrylamide, N-hydroxyethyl (meth) acrylamide, N,N-(dihydroxyethyl) (meth) acrylamide, methyl (meth) acrylate, ethyl (meth) acrylate, propyl (meth) acrylate, isopropyl (meth) acrylate, butyl (meth) acrylate, isobutyl (meth) acrylate, benzyl (meth) acrylate, lauryl (meth) acrylate, 2,3-dibromopropyl (meth) acrylate, 3-(meth) acryloyloxypropyl trimethoxysilane, 11-(meth) acryloyloxyundecyl trimethoxysilane, (meth) acrylamide and the like.

Specific Examples of the polymerizable monomer having two radical polymerizable groups and not containing acidic group include 2,2-bis ((meth) acryloyloxy phenyl) propane, 2,2-bis [4-(3-(meth) acryloyloxy)-2-hydroxy propoxyphenyl] propane (generally called "Bis-GMA"), 2,2-bis (4-(meth) acryloyloxy phenyl) propane, 2,2-bis (4-(meth) acryloyloxy polyethoxyphenyl) propane, 2,2-bis (4-(meth) acryloyloxy diethoxyphenyl) propane, 2,2-bis (4-(meth) acryloyloxy tetraethoxyphenyl) propane, 2,2-bis (4-(meth)) acryloyloxy pentaethoxyphenyl) propane, 2,2-bis (4-(meth) acryloyloxy dipropoxyphenyl) propane, 2-(4-(meth) acryloyloxy diethoxyphenyl)-2-(4-(meth) acryloyloxy diethoxyphenyl) propane, 2-(4-(meth) acryloyloxy diethoxyphenyl)-2-(4-(meth) acryloyloxy ditriethoxyphenyl) propane, 2-(4-(meth) acryloyloxy dipropoxyphenyl)-2-(4-(meth) acryloyloxy triethoxyphenyl) propane, 2,2-bis (4-(meth) acryloyloxy propoxyphenyl) propane, 2,2-bis (4-(meth) acryloyloxy isopropoxyphenyl) propane, 1,4-bis (2-(meth) acryloyloxyethyl) pyromellitate, glycerol di (meth) acrylate, 1-(acryloyloxy)-3-(methacryloyloxy)-2-propanol, ethyleneglycol di (meth) acrylate, diethyleneglycol di (meth) acrylate, triethylene glycol di (meth) acrylate, propylene glycol di (meth) acrylate, butylene glycol di (meth) acrylate, neopentyl glycol di (meth) acrylate, polyethylene glycol di (meth) acrylate, 1,3-butanediol di (meth) acrylate, 1,5-pentanediol di (meth) acrylate, 1,6-hexanediol di (meth) acrylate, 1,10-decanediol di (meth) acrylate, 1,2-bis (3-methacryloyloxy-2-hydroxypropoxy) ethane, 2,2,4-trimethyl hexamethylene bis (2-carbamoyloxy ethyl) dimethacrylate (generally called "UDMA"), 1,2-bis (3-methacryloyloxy-2-hydroxy propoxy) ethane and the like.

Specific Examples of the polymerizable monomer having three or more radical polymerizable groups and not containing acidic group include trimethylolpropane tri (meth) acrylate, trimethylolethane tri (meth) acrylate, trimethylolmethane tri (meth) acrylate, pentaerythritol tri (meth) acrylate, pentaerythritol tetra (meth) acrylate, dipentaerythritol penta (meth) acrylate, N,N-(2,2,4-trimethyl hexamethylene) bis [2-(aminocarboxy) propane-1,3-diol] tetra methacrylate, 1,7-diacryloyloxy-2,2,6,6-tetra acryloyloxymethyl-4-oxyheptane and the like.

For the polymerizable monomer having an acidic group, any polymerizable monomer can be used without any limitation as long as it has one or more polymerizable group and at least one acidic group such as a phosphoric acid group, a pyrophosphoric acid group, a thiophosphoric acid group, a phosphonic acid group, a sulfonic acid group and a carboxylic acid group and the like. It is possible to impart adhesive property with respect to a tooth substance and a prosthetic device by containing a polymerizable monomer having an acidic group.

Specific examples of a phosphoric acid group-containing polymerizable monomer include 2-(meth) acryloyloxyethyl dihydrogen phosphate, 3-(meth) acryloyloxypropyl dihydrogen phosphate, 4-(meth) acryloyloxybutyl dihydrogen phosphate, 5-(meth) acryloyloxypentyl dihydrogen phosphate, 6-(meth) acryloyloxyhexyl dihydrogen phosphate, 7-(meth) acryloyloxyheptyl dihydrogen phosphate, 8-(meth) acryloyloxyoctyl dihydrogen phosphate, 9-(meth) acryloyloxynonyl dihydrogen phosphate, 10-(meth) acryloyloxydecyl dihydrogen phosphate, 11-(meth) acryloyloxyundecyl dihydrogen phosphate, 12-(meth) acryloyloxydodecyl dihydrogen phosphate, 16-(meth) acryloyloxyhexadecyl dihydrogen phosphate, 20-(meth) acryloyloxyicosyl dihydrogen phosphate, bis [2-(meth) acryloyl oxyethyl]hydrogensphosphate, bis [4-(meth) acryloyl oxybutyl] hydrogen phosphate, bis [6-(meth) acryloyl oxyhexyl] hydrogen phosphate, bis [8-(meth) acryloyl oxyoctyl] hydrogen phosphate, bis [9-(meth) acryloyl oxynonyl] hydrogen phosphate, bis [10-(meth) acryloyl oxydecyl] hydrogen phosphate, 1,3-di (meth) acryloyl oxypropyl dihydrogenphosphate, 2-(meth) acryloyl oxyethylphenyl hydrogen phosphate, 2-(meth) acryloyloxyethyl-2-bromoethyl hydrogen phosphate and bis [2-(meth) acryloyloxy-(1-hyrdoxymethyl) ethyl]hydrogen phosphate; acyl chloride, alkali metal salt and ammonium salt thereof; and (meth) acrylamide compound in which the ester bond of these compounds is substituted with an amide bond, and the like.

Specific examples of a pyrophosphoric acid group-containing polymerizable monomer include bis [2-(meth) acryloyl oxyethyl] pyrophosphate, bis [4-(meth) acryloyl oxybutyl] pyrophosphate, bis [6-(meth) acryloyl oxyhexyl] pyrophosphate, bis [8-(meth) acryloyl oxyoctyl] pyrophosphate, bis [10-(meth) acryloyl oxydecyl] pyrophosphate; acyl chloride, alkali metal salt and ammonium salt thereof; and (meth) acrylamide compound in which the ester bond of these compounds is substituted with an amide bond, and the like.

Specific examples of a thiophosphate group-containing polymerizable monomer include 2-(meth) acryloyloxyethyl dihydrogen thiophosphate, 3-(meth) acryloyloxypropyl dihydrogen thiophosphate, 4-(meth) acryloyloxybutyl dihydrogen thiophosphate, 5-(meth) acryloyloxypentyl dihydrogen thiophosphate, 6-(meth) acryloyloxyhexyl dihydrogen thiophosphate, 7-(meth) acryloyloxyheptyl dihydrogen thiophosphate, 8-(meth) acryloyloxyoctyl dihydrogen thiophosphate, 9-(meth) acryloyloxynonyl dihydrogen thiophosphate, 10-(meth) acryloyloxydecyl dihydrogen thiophosphate, 11-(meth) acryloyloxyundecyl dihydrogen thiophosphate, 12-(meth) acryloyloxydodecyl dihydrogen thiophosphate, 16-(meth) acryloyloxyhexadecyl dihydrogen thiophosphate, 20-(meth) acryloyloxyicosyl dihydrogen thiophosphate; acyl chloride, alkali metal salt and ammonium salt thereof; and (meth) acrylamide compound in which the ester bond of these compounds is substituted with an amide bond, and the like. The polymerizable monomer having a thiophosphate group is also classified as a polymerizable monomer having a sulfur atom.

Specific examples of a phosphonic acid group-containing polymerizable monomer include 2-(meth) acryloyloxy ethylphenyl phosphonate, 5-(meth) acryloyloxy pentyl-3-phosphonopropionate, 6-(meth) acryloyloxy hexyl-3-phosphonopropionate, 10-(meth) acryloyloxy decyl-3-phosphonopropionate, 6-(meth) acryloyloxy hexyl-3-phosphonoacetate, 10-(meth) acryloyloxy decyl-3-phosphonoacetate; acyl chloride, alkali metal salt and ammonium salt thereof; and (meth)acrylamide compound in which the ester bond of these compounds is substituted with an amide bond, and the like.

Specific examples of a sulfonic acid group-containing polymerizable monomer include 2-(meth) acrylamide-2-methyl propanesulfonic acid and 2-sulfoethyl (meth) acrylate and the like.

The carboxylic acid group-containing polymerizable monomers are classified into a (meth) acrylic-based compound having one carboxyl group in the molecule and a (meth) acrylic-based compound having a plurality of carboxyl groups in the molecule. Examples of the (meth) acrylic-based compound having one carboxyl group in the molecule include (meth) acrylic acid, N-(meth) acryloyl glycine, N-(meth) acryloyl aspartic acid, 0-(meth) acryloyl tyrosine, N-(meth) acryloyl tyrosine, N-(meth) acryloyl phenylalanine, N-(meth) acryloyl-p-aminobenzoic acid, N-(meth) acryloyl-o-aminobenzoic acid, p-vinylbenzoic acid, 2-(meth) acryloyloxybenzoic acid, 3-(meth) acryloyloxybenzoic acid, 4-(meth) acryloyloxybenzoic acid, N-(meth) acryloyl-5-aminosalicylic acid, N-(meth) acryloyl-4-aminosalicylic acid, 2-(meth) acryloyloxyethyl hydrogen succinate, 2-(meth) acryloyloxyethyl hydrogen phthalate, 2-(meth) acryloyloxyethyl hydrogenmalate; acyl chloride thereof; and (meth)acrylamide compound in which the ester bond of these compounds is substituted with an amide bond, and the like. Examples of the (meth) acrylic-based compound having a plurality of carboxyl groups in the molecule include 6-(meth) acryloyl oxyhexane-1,1-dicarboxylic acid, 9-(meth) acryloyl oxynonane-1,1-dicarboxylic acid, 10-(meth) acryloyl oxydecane-1,1-dicarboxylic acid, 11-(meth) acryloyloxy undecane-1,1-dicarboxylic acid, 12-(meth) acryloyl oxydodecane-1,1-dicarboxylic acid, 13-(meth) acryloyloxy tridecane-1,1-dicarboxylic acid, 4-(meth) acryloyloxyethyl trimeritate, 4-(meth) acryloyloxybutyl trimeritate, 4-(meth) acryloyloxyhexyl trimeritate, 4-(meth) acryloyloxydecyl trimeritate, 2-(meth) acryloyl oxyethyl-3'-(meth) acryloyloxy-2'-(3,4-dicarboxy benzoyloxy) propylsuccinate; acid anhydrides and acid halides thereof; and (meth) acrylamide compound in which the ester bond of these compounds is substituted with an amide bond, and the like.

Preferable examples include 10-methacryloyloxydecyl dihydrogenphosphate and 6-methacryloxyhexyl phosphonoacetate. From the view point of imparting adhesive property, the compounding amount of the polymerizable monomer having an acidic group is, with respect to 100 parts by mass of the total amount of the polymerizable monomer contained in the dental photocurable composition, preferably 1 part by mass or more, more preferably 1 part by mass or more 30 parts by mass or less. When the compounding amount is less than 1 part by mass, there is a case that sufficient adhesive property to tooth substance, metal and metal oxide is not be exhibited. When the compounding amount is more than 30 parts by mass, there is a case that storage stability is lowered.

Specific examples of the polymerizable monomer having an alkoxysilyl gruop include a (meth) acrylic compound and a (meth) acrylamide compound having one alkoxysilyl group in the molecule and a (meth) acrylic compound and a (meth) acrylamide compound having a plurality of alkoxysilyl groups in the molecule. Specific examples include 2-(meth) acryloxyethyl trimethoxysilane, 3-(meth) acryloxypropyl trimethoxysilane, 3-(meth) acryloxypropyl triethoxysilane, 3-(meth) acryloxypropyl methyldimethoxysilane, 4-(meth) acryloxybutyl trimethoxysilane, 5-(meth) acryloxypentyl trimethoxysilane, 6-(meth) acryloxyhexyl trimethoxysilane, 7-(meth) acryloxyheptyl trimethoxysilane, 8-(meth) acryloxyoctyl trimethoxysilane, 9-(meth) acryloxynonyl trimethoxysilane, 10-(meth) acryloxydecyl trimethoxysilane, 11-(meth) acryloxyundecyl trimethoxysilane. Furthermore, specific examples having a urethane group or an ether group include 3,3-dimethoxy-8,37-dioxo-2,9,36-trioxa-7,38-diaza-3-silatetracontan-40-yl (meth) acrylate, 2-((3,3-dimethoxy-8-oxo-2,9,18-trioxa-7-aza-3-silanonadecane-19-oyl) amino)-2-methylpropane-1,3-diyl di (meth) acrylate, 3,3-dimethoxy-8,19-dioxo-2,9,18-trioxa-7, 20-diaza-3-siladocosane-22-yl (meth) acrylate, 3,3-dimethoxy-8,22-dioxo-2,9,12,15,18,21-hexaoxa-7,23-diaza-3-silapentacosane-25-yl (meth) acrylate, 3,3-dimethoxy-8,22-dioxo-2,9,12,15,18,21,26-heptaoxa-7,23-diaza-3-silaoctacosane-28-yl (meth) acrylate, 3,3-dimethoxy-8,19-dioxo-2,9,12,15,18-pentaoxa-7,20-diaza-3-siladocosane-22-yl (meth) acrylate, 3,3-dimethoxy-8,19-dioxo-2,9,12,15, 18,23-hexaoxa-7,20-diaza-3-silapentacosane-25-yl (meth) acrylate, 2-((3,3-dimethoxy-8-oxo-2,9,12,15,18-pentaoxa-7-aza-3-silanonadecane-19-oyl) amino)-2-methylpropan-1, 3-diyldi (meth) acrylate, 4,4-diethoxy-17-oxo-3,16,21-trioxa-18-aza-4-silatricosane-23-yl (meth) acrylate, 4,4-diethoxy-17-oxo-3,16,21,24-tetraoxa-18-aza-4-silahexacosane-26-yl (meth) acrylate, 4,4-diethoxy-13-oxo-3,12,17-trioxa-14-aza-4-silanonadecane-19-yl (meth) acrylate, 4,4-diethoxy-17-oxo-3,16-dioxa-18-aza-4-silaicosane-20-yl (meth) acrylate and 2-methyl-2-((11-(triethoxysilyl) undecyloxy) carbonylamino) propan-1,3-diyldi (meth) acrylate.

The dental photocurable composition of the present disclosure may contain a polymerizable monomer having a sulfur atom as the (A) polymerizable monomer in order to impart adhesive property with respect to a noble metal. As the polymerizable monomer having a sulfur atom, any known compound can be used without any limitation as long as it is a polymerizable monomer having one or more sulfur atoms and a polymerizable group. Specifically, it refers to a compound having a partial structure such as —SH, —S—S—, >C=S, >C—S—C<, >P=S, or a compound prepared by tautomerism. Specific examples include 10-methacryloxy decyl-6,8-dithiooctanate, 6-methacryloxy hexyl-6,8-dithiooctanate, 6-methacryloxy hexyl-2-thiouracil-5-carboxylate, 2-(11-methacryloxy undecylthio)-5-mercapto-1,3, 4-thiadiazole, 10-(meth) acryloxy decyl dihydrogenthiophosphate.

An oligomer or a prepolymer having at least one polymerizable group in its molecule may be used other than such a polymerizable monomer, without any limitation. There is no problem even if a substituent such as a fluoro group is contained in the same molecule. The polymerizable monomers described above can be used not only singly but also in combinations of a plurality thereof.

The dental photocurable composition of the present disclosure may contain a silane coupling agent as the (A) polymerizable monomer in order to impart adhesive property with respect to glass ceramics. Any known silane coupling agent can be used without any limitation, but 3-methacryloxypropyl trimethoxysilane, 8-methacryloxyoctyl trimethoxysilane, and 11-methacryloxyundecyl trimethoxysilane are preferable. From the viewpoint of imparting adhesive property, the compounding amount is, with respect to 100 parts by mass of the total amount of the polymerizable monomer contained in the composition, preferably 1 part by mass or more, more preferably 5 parts by mass or more and less than 20 parts by mass. Since the purpose of the silane coupling agent as a polymerizable monomer is to impart adhesive property with respect to glass ceramics or a resin material containing a filler consisting of glass ceramics, the silane coupling agent is compounded separately from the surface treatment agent of the filler.

The dental photocurable composition of the present disclosure may contain a polymerizable monomer having a sulfur atom as the (A) polymerizable monomer in order to impart adhesive property with respect to a noble metal. From the view point of imparting adhesive property, the compounding amount of the polymerizable monomer having a sulfur atom is, with respect to 100 parts by mass of the total amount of the polymerizable monomer contained in the dental photocurable composition, 0.01 part by mass or more, preferably 0.1 parts by mass or more and less than 20 parts by mass.

<Photopolymerization Initiator>

The photopolymerization initiator used in the dental photocurable composition of the present disclosure includes (B) photosensitizer, and (D) photopolymerization accelerator, and may include (C) photoacid generator, and these are not particularly limited, and any known compounds commonly used may be used without any limitation.

[(B) Photosensitizer]

Specific examples of the (B) photosensitizer which can be used in the present disclosure include α-diketones such as benzil, camphorquinone, camphorquinone carboxylic acid, camphorquinone sulfonic acid, α-naphthyl, acetonaphthene, p,p'-dimethoxybenzyl, p,p'-dichlorobenzylacetyl, pentanedion, 1,2-phenanthrenequinone, 1,4-phenanthrenequinone, 3,4-phenanthrenequinone, 9,10-phenanthrenequinone and naphthoquinone; benzoin alkyl ethers such as benzoin, benzoin methyl ether and benzoin ethyl ether; thioxanthones such as thioxanthone, 2-chlorothioxanthone, 2-methylthioxanthone, 2-isopropylthioxanthone, 2-methoxythioxanthone, 2-hydroxythioxanthone, 2,4-diethylthioxanthone and 2,4-diisopropylthioxanthone; benzophenones such as benzophenone, p-chlorobenzophenone and p-methoxybenzophenone; acylphosphine oxides such as bis (2,6-dimethoxy benzoyl) phenylphosphine oxide, bis (2,6-dimethoxy benzoyl) (2,4,4-trimethyl pentyl) phosphine oxide, bis (2,6-dimethoxy benzoyl)-n-butylphosphine oxide, bis (2,6-dimethoxy benzoyl)-(2-methylprop-1-yl) phosphine oxide, bis (2,6-dimethoxy benzoyl)-(1-methylprop-1-yl) phosphine oxide, bis (2,6-dimethoxy benzoyl)-t-butyl phosphine oxide, bis (2,6-dimethoxy benzoyl) cyclohexyl phosphine oxide, bis (2,6-dimethoxy benzoyl) octyl phosphine oxide, bis (2-methoxy benzoyl) (2-methylprop-1-yl) phosphine oxide, bis (2-methoxy benzoyl) (1-methylprop-1-yl) phosphine oxide, bis (2,6-diethoxy benzoyl) (2-methylprop-1-yl) phosphine oxide, bis (2,6-diethoxy benzoyl) (1-methylprop-1-yl) phosphine oxide, bis (2,6-dibutoxy benzoyl) (2-methylprop-1-yl) phosphine oxide, bis (2,4-dimethoxy benzoyl) (2-methylprop-1-yl) phosphine oxide, bis (2,4,6-trimethyl benzoyl) phenyl phosphine oxide, 2,4,6-trimethyl benzoyl diphenyl phosphine oxide, bis (2,4,6-trimethyl benzoyl) (2,4-dipentoxy phenyl) phosphine oxide, bis (2,6-dimethoxy benzoyl) benzyl phosphine oxide, bis (2,6-dimethoxy benzoyl)-2-phenylpropyl phosphine oxide, bis (2,6-dimethoxy benzoyl)-2-phenylethyl phosphine oxide, bis (2,6-dimethoxy benzoyl) benzyl phosphine oxide, bis (2,6-dimethoxy benzoyl)-2-phenylpropyl phosphine oxide, bis (2,6-dimethoxy benzoyl)-2-phenylethyl phosphine oxide, 2,6-dimethoxy benzoyl benzyl butyl phosphine oxide, 2,6-dimethoxy benzoyl benzyl octyl phosphine oxide, bis (2,4,6-trimethyl benzoyl) isobutyl phosphine oxide and 2,6-dimethoxy benzoyl-2,4,6-trimethyl benzoyl-n-butyl phosphine oxide; acylgermanium compounds such as bisbenzoyl diethylgermanium, bisbenzoyl dimethylgermanium, bisbenzoyl dibutylgermanium, bis (4-methoxybenzoyl) dimethylgermanium and bis (4-methoxybenzoyl) diethylgermanium; α-aminoacetophenones such as 2-benzyl-dimethylamino-1-(4-morpholinophenyl)-butanone-1, and 2-benzyl-diethylamino-1-(4-morpholinophenyl)-propanone-1; ketals such as benzyl dimethyl ketal, benzyl diethyl ketal and benzyl (2-methoxyethyl ketal); and titanocenes such as bis (cyclopentadienyl)-bis [2,6-difluoro-3-(1-pyrrolyl) phenyl]-titanium, bis (cyclopentadienyl)-bis (pentanefluorophenyl)-titanium and bis (cyclopentadienyl)-bis (2,3,5,6-tetrafluoro-4-disiloxyphenyl)-titanium.

The photosensitizer (B) may be appropriately selected according to the wavelength, the intensity and the irradiation time of light used for polymerization, and the type and the compounding amount of other components to be combined. In addition, the photosensitizer may be used not only singly but also in combinations of two or more. Among them, α-diketone compounds having a maximum absorption wavelength in the visible light region are preferably used, and camphorquinone compounds such as camphorquinone, camphorquinone carboxylic acid and camphorquinone sulfonic acid are more preferable. Camphorquinone is particularly preferred because it is easily available.

Usually, the compounding amount of the (B) photosensitizer with respect to 100 parts by mass of the total amount of the (A) polymerizable monomer contained in the dental photocurable composition is preferably 0.02 to 1 parts by mass, more preferably 0.02 to 0.5 parts by mass. When the compounding amount of the photosensitizer is less than 0.02 parts by mass, there is a case that the polymerization activity with respect to the irradiation light is poor and the curing becomes insufficient. When the compounding amount is more than 1 part by mass, there is a case that although sufficient curability is exhibited, the sensitivity to light is shortened, and yellowness is increased.

The dental photocurable composition of the present disclosure may contain only the α-diketone compound as the (B) photosensitizer.

[(C) Photoacid Generator]

As the (C) photoacid generator which can be used in the dental photocurable composition of the present disclosure, known compounds can be used without limitation. Specific examples include triazine compounds, iodonium salt compounds, sulfonium salt compounds, and sulfonic acid ester compounds. Among these, triazine compounds and iodonium salt-based compounds are preferable because of having high polymerizability in the case of using in combination with a sensitizer. Iodonium salt-based compounds are more preferable. Iodonium-based salt compounds are susceptible to sensitization by photosensitizers that have absorption in the visible light region.

Specific examples of the triazine compound include 2,4,6-tris (trichloro methyl)-s-triazine, 2,4,6-tris (tribromo methyl)-s-triazine, 2-methyl-4,6-bis (trichloro methyl)-s-triazine, 2-methyl-4,6-bis (tribromo methyl)-s-triazine, 2-phenyl-4,6-bis (trichloro methyl)-s-triazine, 2-(p-methoxy phenyl)-4,6-bis (trichloro methyl)-s-triazine, 2-(p-methyl thiophenyl)-4,6-bis (trichloro methyl)-s-triazine, 2-(p-chloro phenyl)-4,6-bis (trichloro methyl)-s-triazine, 2-(2,4-dichloro phenyl)-4,6-bis (trichloro methyl)-s-triazine, 2-(p-bromo phenyl)-4,6-bis (trichloro methyl)-s-triazine, 2-(p-tolyl)-4,6-bis (trichloro methyl)-s-triazine, 2-n-propyl-4,6-bis (trichloro methyl)-s-triazine, 2-(α,α,β-trichloro ethyl)-4,6-bis (trichloro methyl)-s-triazine, 2-styryl-4,6-bis (trichloro methyl)-s-triazine, 2-[2-(p-methoxy phenyl) ethenyl]-4,6-bis (trichloro methyl)-s-triazine, 2-[2-(o-methoxy phenyl) ethenyl]-4,6-bis (trichloro methyl)-s-triazine, 2-[2-(p-butoxy phenyl) ethenyl]-4,6-bis (trichloro methyl)-s-triazine, 2-[2-(3,4-dimethoxy phenyl) ethenyl]-4,6-bis (trichloro methyl)-s-triazine, 2-[2-(3,4,5-trimethoxy phenyl) ethenyl]-4,6-bis (trichloro methyl)-s-triazine, 2-(1-naphthyl)-4,6-bis (trichloro methyl)-s-triazine, 2-(4-biphenylyl)-4,6-bis (trichloro methyl)-s-triazine, 2-[2-{N,N-bis(2-hydroxy ethyl) amino} ethoxy]-4,6-bis (trichloro methyl)-s-triazine, 2-[2-{N-hydroxy ethyl-N-ethylamino} ethoxy]-4,6-bis (trichloro methyl)-s-triazine, 2-[2-{N-hydroxy ethyl-N-methylamino} ethoxy]-4,6-bis (trichloro methyl)-s-triazine, 2-[2-{N,N-diallyl amino} ethoxy]-4,6-bis (trichloro methyl)-s-triazine and the like. Among them, 2,4,6-tris (trichloro methyl)-s-triazine is preferable.

Any iodonium salt-based compound can be used as long as it is known. For the specific examples, the structural formula of the iodonium salt-based compound can be represented by the following formula (2).

$$[(R_1)_2I]^+[A]^- \quad \text{[Formula (2)]}$$

(In the formula, $[(R_1)_2I]^+$ is a cation part, $[A]^+$ is an anion part, R1 shown in the formula (2) represents an organic group bonded to I, and R1s may be the same or different. R1 represents, for example, an aryl group having 6 to 30 carbon atoms, a heterocyclic group having 4 to 30 carbon atoms, an alkyl group having 1 to 30 carbon atoms, an alkenyl group having 2 to 30 carbon atoms, or an alkynyl group having 2 to 30 carbon atoms, which may have at least one substituted group selected from the group consisting of groups such as alkyl, hydroxy, alkoxy, alkylcarbonyl, arylcarbonyl, alkoxycarbonyl, aryloxycarbonyl, arylthiocarbonyl, acyloxy, arylthio, alkylthio, aryl, heterocycle, aryloxy, alkylsulfinyl, arylsulfinyl, alkylsulfonyl, arylsulfonyl, alkyleneoxy, amino, cyano, nitro groups and halogens.)

In the above, examples of the aryl group having 6 to 30 carbon atoms include a monocyclic aryl group such as a phenyl group and a condensed polycyclic aryl group such as a naphthyl, anthrasenyl, phenanthrenyl, pyrenyl, chrysenyl, naphthacenyl, benzanthrasenyl, anthraquinolyl, fluorenyl, naphthoquinone and anthraquinone.

Examples of the heterocyclic group having 4 to 30 carbon atoms include cyclic groups containing 1 to 3 heteroatoms such as oxygen, nitrogen, and sulfur, which may be the same or different. Specific examples include a monocyclic heterocyclic group such as thienyl, furanyl, pyranyl, pyrrolyl, oxazolyl, thiazolyl, pyridyl, pyrimidyl and pyrazinyl, and a condensed polycyclic heterocyclic group such as indolyl, benzofuranyl, isobenzofuranyl, benzothienyl, isobenzothienyl, quinolyl, isoquinolyl, quinoxalinyl, quinazolinyl, carbazolyl, acridinyl, phenothiazinyl, phenazinyl, xanthenyl, thianthrenyl, phenoxazinyl, phenoxathiinyl, chromanyl, isochromanyl, dibenzothienyl, xanthonyl, thioxanthonyl and dibenzofuran.

Specific examples of alkyl groups having 1 to 30 carbon atoms include a linear alkyl group such as methyl, ethyl, propyl, butyl, hexadecyl and octadecyl, a branched alkyl group such as isopropyl, isobutyl, sec-butyl, tert-butyl, isopentyl, neopentyl, tert-pentyl, isohexyl and a cycloalkyl groups such as cyclopropyl, cyclobutyl, cyclopentyl and cyclohexyl.

In addition, specific examples of the alkenyl group having 2 to 30 carbon atoms include a linear chain or branched group such as vinyl, allyl, 1-propenyl, isopropenyl, 1-butenyl, 2-butenyl, 3-butenyl and 1-methyl-1-propenyl.

Further, specific examples of the alkynyl group having 2 to 30 carbon atoms include a linear chain or branched group such as ethynyl, 1-propynyl, 2-propynyl, 1-butynyl, 2-butynyl, 3-butynyl, 1-methyl-1-propynyl and 1-methyl-2-propynyl.

The above-described aryl group having 6 to 30 carbon atoms, heterocyclic group having 4 to 30 carbon atoms, alkyl group having 1 to 30 carbon atoms, alkenyl group having 2 to 30 carbon atoms and alkynyl group having 2 to 30 carbon atoms may have at least one substituted group. Specific examples of the substituted group include a linear alkyl group having 1 to 18 carbon atoms such as methyl, ethyl, propyl, butyl and octadecyl; a branched alkyl group having 1 to 18 carbon atoms such as isopropyl, isobutyl, sec-butyl and tert-butyl; a cycloalkyl group having 3 to 18 carbon atoms such as cyclopropyl, cyclobutyl, cyclopentyl and cyclohexyl; a hydroxy group; a linear chain or branched alkoxy group having 1 to 18 carbon atoms such as methoxy, ethoxy, propoxy, isopropoxy, butoxy, isobutoxy, sec-butoxy, tert-butoxy and dodecyloxy; a linear chain or branched alkylcarbonyl group having 2 to 18 carbon atoms such as acetyl, propionyl, butanoyl, 2-methylpropionyl, heptanoyl, 2-methylbutanoyl, 3-methylbutanoyl and octanoyl; an arylcarbonyl group having 7 to 11 carbon atoms such as benzoyl and naphthoyl; a linear chain or branched alkoxycarbonyl group having 2 to 19 carbon atoms such as methoxycarbonyl, ethoxycarbonyl, propoxycarbonyl, isopropoxycarbonyl, butoxycarbonyl, isobutoxycarbonyl, sec-butoxycarbonyl and tert-butoxycarbonyl; an aryloxycarbonyl group having 7 to 11 carbon atoms such as phenoxycarbonyl and naphthoxycarbonyl; an arylthiocarbonyl group having 7 to 11 carbon atoms such as phenylthiocarbonyl and naphthoxythiocarbonyl; a linear chain or branched acyloxy group having 2 to 19 carbon atoms such as acetoxy, ethylcarbonyloxy, propylcarbonyloxy, isobutylcarbonyloxy, sec-butylcarbonyloxy, tert-butylcarbonyloxy and octadecylcarbonyloxy; an arylthio group having 6 to 20 carbon atoms such as phenylthio, biphenylthio, methylphenylthio, chlorophenylthio, bromophenylthio, fluorophenylthio, hydroxyphenylthio, methoxyphenylthio, naphthylthio, 4-[4-(phenylthio) benzoyl]phenylthio, 4-[4-(phenylthio) phenoxy] phenylthio, 4-[4-(phenylthio) phenyl] phenylthio, 4-(phenylthio) phenylthio, 4-benzoyl phenylthio, 4-benzoyl-chlorophenylthio, 4-benzoyl-methylthio phenylthio, 4-(methylthiobenzoyl) phenylthio and 4-(p-tert-butylbenzoyl) phenylthio; a linear chain or branched alkylthio group having 1 to 18 carbon atoms such as methylthio, ethylthio, propylthio, tert-butylthio, neopentylthio and dodecylthio; an aryl group having 6 to 10 carbon atoms such as phenyl, tolyl, dimethylphenyl and naphthyl; a heterocycle group having 4 to 20 carbon atoms such as thienyl, furanyl, pyranyl, xanthenyl, chromanyl, isochromanyl, xanthonyl, thioxanthonyl and dibenzofuranyl; an aryloxy group having 6 to 10 carbon atoms such as phenoxy and naphthyloxy; a linear chain or branched alkylsulfinyl group having 1 to 18 carbon atoms such as methylsulfinyl, ethylsulfinyl, propylsulfinyl, tert-pentylsulfinyl and octylsulfinyl; an arylsulfinyl group having 6 to 10 carbon atoms such as phenylsulfinyl, tolylsulfinyl and naphthylsulfinyl; a linear chain or branched alkylsulfonyl group having 1 to 18 carbon atoms such as methylsulfonyl, ethylsulfonyl, propylsulfonyl, isopropylsulfonyl, butylsulfonyl and octylsulfonyl; an arylsulfonyl group having 6 to 10 carbon atoms such as phenylsulfonyl, tolylsulfonyl (tosyl), naphthylsulfonyl; an alkyleneoxy groups; a cyano groups; a nitro groups; and halogens such as fluorine, chlorine, bromine and iodine.

Among the iodonium salt-based compounds, the aryl iodonium salt is preferable because of having high stability. Further, it is preferable that the aryl group has a substituent in order to improve the solubility to the photopolymerization composition. Specifically, a linear alkyl group such as methyl, propyl, octyl, decyl, undecyl, dodecyl and tridecyl, a branched alkyl group such as isopropyl, isobutyl, sec-butyl, tert-butyl, isopentyl, neopentyl, tert-pentyl and isohexyl, a functional group in which one or more of H of these is substituted with F, a perfluoroalkyl group and halogen is suitable as the substituent.

The structure of an anion portion of the iodonium salt-based compound is not particularly limited, and examples include those having atoms such as halogen, P, S, B, Al and Ga. From the viewpoint of safety, anions having As or Sb can be used, but they are not preferable in dental applications. Further, the anion preferably has an organic group such as an alkyl group and/or an alkoxy group and/or an aryl group, and further, most preferably has an organic group such as an alkyl group and/or an alkoxy group and/or an aryl group, in which at least one H is substituted with F. Since the iodonium salt-based compound having such an anion has high solubility in the dental photocurable composition, it is expected to preventing precipitation during low-temperature storage or long-term storage and to shorten the time for preparing due to dissolving in the composition in a short time. Further, an iodonium salt-based compound of an anion having an organic group such as an alkyl group and/or an alkoxy group and/or an aryl group, in which at least one H is substituted with F can be expected to have higher solubility. When the photoacid generator is precipitated, there is a case that it may cause a decrease in color stability after irradiation and a decrease in flexural strength, and therefore it is not preferable. As the anion having an organic group such as an alkyl group and/or an alkoxy group and/or an aryl group, in which at least one H is substituted with F, an anion having any atom can be used. However, from the viewpoint of versatility and safety, those having one or more of P, S, B, Al and Ga are preferable.

Examples of the anion having no alkyl group and/or alkoxy group and/or aryl group include halogens such as chloride and bromide, perhalonic acids such as perchloric acid, aromatic sulfonic acids such as p-toluenesulfonate, camphorsulfonnic acids, nitrates, acetates, chloroacetates, carboxylates, phenolates, tetrafluoroborates, hexafluorophosphates, hexafluoroantimonates, hexafluoroarsenates and the like. Among these, p-toluenesulfonate, camphorsulfonic acid and carboxylate are preferably used.

Since the anionic part of [A]⁻ of the iodonium salt-based compound of the formula (2) improves the solubility to the dental photocurable composition, it is preferable that the anion has an organic group such as alkyl group and/or alkoxy group and/or aryl group, in which at least one His substituted with F. Specifically, the number of carbon atoms of the alkyl group in the anion part of [A]⁻ of the iodonium salt-based compound of the formula (2) is 1 to 8, and preferably 1 to 4. Specific examples include a linear alkyl group such as methyl, ethyl, propyl, butyl, pentyl and octyl, a branched alkyl group such as isopropyl, isobutyl, sec-butyl and tert-butyl, and a cycloalkyl group such as cyclopropyl, cyclobutyl, cyclopentyl and cyclohexyl. The ratio (F/H) of the number of hydrogen atoms to fluorine atoms in the alkyl group is 4 or more, and the ratio (F/H) of the number of hydrogen atoms to fluorine atoms in the alkyl group is preferably 9 or more. More preferably, all hydrogen atoms of the hydrocarbon are substituted with fluorine. An iodonium salt consisting of an anion having an alkyl group having a different ratio of a hydrogen atom and a fluorine atom may be compounded in the dental photocurable composition.

Further, specific examples of the alkyl group include a linear chain or branched perfluoroalkyl group such as $CF_3$, $CF_3CF_2$, $(CF_3)_2CF$, $CF_3CF_2CF_2$, $CF_3CF_2CF_2CF_2$, $(CF_3)_2CFCF_2$, $CF_3CF_2(CF_3)CF$ and $(CF_3)_3C$.

The number of carbon atoms of the alkyl group in the anion part of [A]⁻ of the iodonium salt-based compound of the formula (2) is 1 to 8, and preferably 1 to 4. Specific examples include a linear alkoxy group such as methoxy, ethoxy, propoxy, butoxy, pentoxy and octoxy, and a branched alkoxy group such as isopropoxy, isobutoxy, sec-butoxy and tert-butoxy. The ratio (F/H) of the number of hydrogen atoms to fluorine atoms in the alkyl group is 4 or more, and the ratio (F/H) of the number of hydrogen atoms to fluorine atoms in the alkyl group is preferably 9 or more. More preferably, all hydrogen atoms of the hydrocarbon are substituted with fluorine. An iodonium salt consisting of an anion having an alkoxy group having a different ratio of a hydrogen atom and a fluorine atom may be compounded in the dental photocurable composition.

Further, specific examples of the alkoxy group include a linear or branched perfluoroalkoxy group such as $CF_3O$, $CF_3CF_2O$, $CF_3CF_2CF_2O$, $(CF_3)_2CFO$, $CF_3CF_2CF_2CF_2O$, $(CF_3)_2CFCF_2O$, $CF_3CF_2(CF_3)CFO$, $CF_3CF_2CF_2CF_2CF_2O$ and $CF_3CF_2CF_2CF_2CF_2CF_2CF_2CF_2O$.

The phenyl group in the anion part of [A]⁻ of the iodonium salt compound of the formula (2) may be a phenyl group, in which at least one H is substituted with fluorine atom, an alkyl group and/or an alkoxy group substituted with fluorine atom. The alkyl group and/or alkoxy group substituted with fluorine atom are preferably those described above. Specific examples of particularly preferable phenyl group include perfluorophenyl group such as pentafluorophenyl group ($C_6F_5$), trifluorophenyl group ($C_6H_2F_3$), tetrafluorophenyl group ($C_6HF_4$), trifluoromethylphenyl group ($CF_3C_6H_4$), bis (trifluoromethyl) phenyl group (($CF_3)_2C_6H_3$), pentafluoroethyl phenyl group ($CF_3CF_2C_6H_4$), bis (pentafluoroethyl) phenyl group (($CF_3)_2C_6H_3$), trifluoromethyl fluorophenyl group ($CF_3C_6H_3F$), bistrifluoromethyl fluorophenyl group (($CF_3)_2C_6H_2F$), pentafluoroethyl fluorophenyl group ($CF_3CF_2C_6H_3F$), bispentafluoroethyl fluorophenyl group ($CF_3CF_2)_2C_6H_2F$ and the like. An iodonium salt consisting of an anion having a phenyl group having a different ratio of a hydrogen atom and a fluorine atom may be compounded in the dental photocurable composition.

As specific examples of the anion portion of [A]⁻ of the iodonium salt compound of the formula (2), examples of the anion having P include $[(CF_3CF_2)_3PF_3]^-$, $[(CF_3CF_2CF_2)_3PF_3]^-$, $[((CF_3)_2CF)_2PF_4]^-$, $[((CF_3)_2CF)_3PF_3]^-$, $[((CF_3)_2CF)_4PF_2]^-$, $[((CF_3)_2CFCF_2)_2PF_4]^-$, $[((CF_3)_2CFCF_2)_3PF_3]^-$ and the like. Examples of the anion having S include $[(CF_3SO_2)_3C]^-$, $[(CF_3CF_2SO_2)_3C]^-$, $[(CF_3CF_2CF_2SO_2)_3C]^-$, $[(CF_3CF_2CF_2CF_2SO_2)_3C]^-$, $[CF_3CF_2CF_2CF_2SO_3]^-$, $[CF_3CF_2CF_2SO_3]^-$, $[(CF_3CF_2SO_2)_3C]^-$, $[(SO_2CF_3)_3N]^-$, $[(SO_2CF_2CF_3)_2N]^-$, $[((CF_3)C_6H_4)SO_3]^-$, $[SO_3(CF_2CF_2CF_2CF_2)SO_3]^{2-}$ and the like. Examples of the anion having B include $[B(C_6F_5)_4]^-$, $[(C_6H_5)B((CF_3)_2C_6H_3)_3]^-$, $[(C_6H_5)B(C_6F_5)_3]^-$ and the like. Examples of an anion having Ga include $[((CF_3)_4Ga)]^-$, $[Ga(C_6F_5)_4]^-$ and the like. Examples of anions having Al include $[((CF_3)_3CO)_4Al]^-$, $[((CF_3CF_2)_3CO)_4Al]^-$.

The compounding amount of the (C) photoacid generator in the case that the dental photocurable composition of the present disclosure contains the (C) photoacid generator is preferably 0.1 to 10 parts by mass or more, more preferably 0.2 to 5 parts by mass or more, with respect to 100 parts by mass of the total amount of the (A) polymerizable monomer. When the compounding amount of the photoacid generator is less than 0.1 parts by mass, there is a case that expected polymerization promoting ability is not exhibited and the curing becomes insufficient. When the compounding amount is more than 10 parts by mass, although sufficient curability is exhibited, there is a case that the sensitivity to light is lowered to shorten working time, and discoloration such as browning of the cured body increases.

The photoacid generator that can be used in the dental photocurable composition of the present disclosure is not limited to the photoacid generator described in the specific example, and two or more types can be used in combination.

The dental photocurable composition of the present disclosure may comprise only an aryl iodonium salt which is a salt of an anion having an organic group and one or more atoms of P, B, Al, S, and Ga, and an aryl iodonium cation as the (C) photoacid generator. The dental photocurable composition of the present disclosure may comprise only an aryl iodonium salt which is a salt of an anion having an organic group in which at least one H may be substituted with F and one or more atoms of P, B, Al, S, and Ga, and an aryl iodonium cation as the (C) photoacid generator.

[(D) Photopolymerization Accelerator]

The (D) photopolymerization accelerator which is used for the dental photocurable composition of the present disclosure is not particularly limited as long as it has polymerization promoting ability, and any known photopolymerization accelerator commonly used in the dental field may be used without any limitation. As the (D) photopolymerization accelerator, a primary to tertiary amine compound such as an aromatic amine compound and an aliphatic amine compound, an organic metal compound, a phosphine compound and the like can be used. Among these, a tertiary aliphatic amine compound and an organic metal compound are preferable because of having good color stability after irradiation.

Aromatic amine compound refers to a compound in which one or more H of ammonia ($NH_3$) is replaced with an aromatic ring. Aromatic amine compound in which one H of $NH_3$ is substituted with an aromatic ring is classified into an aromatic primary amine compound, aromatic amine compound in which one H of $NH_3$ is substituted with an aromatic ring and one H of remaining two H is substituted with an aromatic ring or an alkyl group is classified into an aromatic secondary amine compound, and aromatic amine compound in which one H of $NH_3$ is substituted with an aromatic ring and remaining two H are substituted with an aromatic ring or an alkyl group is classified into an aromatic tertiary amine compound.

Specific examples of the aromatic primary amine compound include aniline. Specific examples of the aromatic secondary amine compound include N-protected amino acid (ester) such as N-phenyl benzylamine, N-benzyl-p-anisidine, N-benzyl-o-phenetidine, N-phenylglycine ethyl and N-phenylglycine. Specific examples of the aromatic tertiary amine compound include N,N-dimethylaniline, N,N-diethylaniline, N,N-di-n-butylaniline, N,N-dibenzylaniline, p-N,N-dimethyl-toluidine, m-N,N-dimethyl-toluidine, p-N,N-diethyl-toluidine, p-bromo-N,N-dimethylaniline, m-chloro-N,N-dimethylaniline, p-dimethylamino benzaldehyde, p-dimethylamino acetophenone, p-dimethylamino benzoic acid, p-dimethylamino benzoic acid ethyl ester, p-dimethylamino benzoic acid isoamyl estel, p-dimethylamino benzoic acid 2-butoxyethyl, p-dimethylamino benzoic acid 2-ethylhexyl, p-dimethylamino benzoic acid amino ester, N,N-dimethyl anthranic acid methyl ester, N,N-dihydroxyethyl aniline, N,N-diisopropanol aniline, p-N,N-dihydroxyethyl-toluidine, p-N,N-dihydroxypropyl-toluidine, p-dimethylamino phenyl alcohol, p-dimethylamino styrene, N,N-dimethyl-3,5-xylidine, 4-dimethylamino pyridine, N,N-dimethyl-α-naphthylamine, N,N-dimethyl-8-naphthylamine and the like. Among them, p-dimethylaminobenzoic acid ethyl ester is preferable.

Specific examples of the above organic metal compound include an organic metal compound containing scandium (Sc), titanium (Ti), vanadium (V), manganese (Mn), iron (Fe), cobalt (Co), nickel (Ni), copper (Cu), tin (Sn), zinc (Zn) an/or zirconia (Zr), and an organic metal compound containing tin (Sn), vanadium (V) and/or copper (Cu) is preferable. Specific examples of the organic metal compound containing tin (Sn) include dibutyl-tin-diacetate, dibutyl-tin-dimaleate, dioctyl-tin-dimaleate, dioctyl-tin-dilaurate, dibutyl-tin-dilaurate, dioctyl-tin-diversate, dioctyl-tin-S,S'-bis-isooctyl mercapto acetate, tetramethyl-1,3-diacetoxy distanoxane and the like. Specific examples of the organic metal compound containing vanadyl (V) include acetylacetone vanadium, divanadium tetraoxide, vanadyl acetylacetonate, vanadyl stearate oxide, vanadyl oxalate, vanadyl sulphate, oxobis (1-phenyl-1,3-butandionate) vanadium, bis (maltlate) oxovanadium, vanadium pentoxide and sodium metavanadate. Specific examples of the organic metal compound containing copper (Cu) include copper acetylacetone, copper naphthenate, copper octylate, copper stearate and copper acetate.

The phosphine compound refers to a compound which is trisubstituted on P atom with organic groups, and the aromatic phosphine compound refers to a compound which is substituted on P atom with a phenyl group which may have one or more substituents. Specific examples of the phosphine compound include trimethylphosphine, tributylphosphine, trihexylphosphine, tri-n-octylphosphine, tricyclohexylphosphine, tri (2-thienyl) phosphine, diphenylpropyl phosphine, di-tert-butyl (3-methyl-2-butenyl) phosphine, methyldiphenyl phosphine, triphenyl phosphine, 2-(diphenylphosphino) styrene, 3-(diphenylphosphino) styrene, 4-(diphenylphosphino) styrene, allyldiphenyl phosphine, 2-(diphenylphosphino) benzaldehyde, 3-(diphenylphosphino) benzaldehyde, 4-(diphenylphosphino) benzaldehyde, 2-(phenylphosphine) benzoic acid, 3-(phenylphosphino) benzoic acid, 4-(phenylphosphino) benzoic acid, tris (2-methoxyphenyl) phosphine, tris (3-methoxyphenyl) phosphine, tris (4-methoxyphenyl) phosphine, 2-(diphenylphosphino) biphenyl, tris (4-fluorophenyl) phosphine, tri (o-trill) phosphine, tri (m-trill) phosphine, tri (p-trill) phosphine, 2-(dimethylamino) phenyldiphenyl phosphine, 3-(dimethylamino) phenyldiphenyl phosphine, 4-(dimethylamino) phenyldiphenyl phosphine, 2,2'-bis (diphenylphosphino) biphenyl, bis [2-(diphenylphosphino) phenyl] ether and the like. Among them, triphenylphosphine, 4-(phenylphosphino) benzoic acid, tri (o-tolyl) phosphine, tri (m-tolyl) phosphine and tri (p-tolyl) phosphine are preferable.

Aliphatic amine compounds refer to compounds in which one or more H of ammonia ($NH_3$) are substituted with alkyl group. As for the alkyl group, $CH_3$— and —$CH_2$— are classified as a primary alkyl group, the one in which one H of —$CH_2$— is substituted with a substituent is classified as a secondary alkyl group, and the one in which two H of —$CH_2$— are substituted with substituents is classified as a tertiary alkyl group. Aliphatic amine in which one H of $NH_3$ is substituted with an alkyl group is classified into an aliphatic primary amine compound, aliphatic amine compound in which two H of $NH_3$ are substituted with an alkyl group is classified into an aliphatic secondary amine compound, and aliphatic amine compound in which three H of $NH_3$ are substituted with an alkyl group is classified into an aliphatic tertiary amine compound.

Specific examples of the aliphatic primary amine compound include amino acid or amino acid ester such as benzhydrylamine, triphenylmethylamine and glycine. Specific examples of the aliphatic secondary amine compound include dibenzylamine, N-benzyl-1-phenylethylamine, bis (1-phenylethyl) amine, bis (4-cyanobenzyl) amine, N-benzyl protected amino acid and N-benzyl protected amino acid ester. Specific examples of the aliphatic tertiary amine compound include tributylamine, tripropylamine, triethylamine, N,N-dimethyl hexylamine, N,N-dimethyl dodecylamine, N,N-dimethyl stearylamine, N-[3-(dimethylamino) propyl] acrylamide, N,N-dimethyl formamide dimethylacetal, N,N-dimethylacetamide dimethylacetal, N,N-dimethylformamide diethylacetal, N,N-dimethylformamide dipropylacetal, N,N-dimethylformamide di-tert-butylacetal, 1-(2-hydroxyethyl) ethyleneimine, N,N-dimethyl ethanolamine, N,N-dimethyl isopropanolamine, N,N-diisopropyl ethanolamine, N-methyl diethanolamine, N-ethyl diethanolamine, N-ethyl diethanolamine, N-butyl diethanolamine, N-lauryl diethanolamine, N-stearyl diethanolamine, triethanolamine, triisopropanolamine, tribenzylamine, dibenzylglycine ethylester, N'-(2-hydroxyethyl)-N,N,N'-trimethylethylene diamine, 2-(dimethylamino)-2-methyl-1-propanol, N,N-dimethyl-2,3-dihydroxypropylamine, N,N-diethylethanolamine, 1-methyl-3-pyrrolidinol, 1-(2-hydroxyethyl) pyrrolidine, 1-isopropyl-3-pyrrolidinol, 1-piperidin ethanol, 2-[2-(dimethylamino) ethoxy] ethanol, N,N-dimethylglycine, N,N-dimethylglycine methyl, N,N-diethylglycine methyl, N,N-dimethylglycine ethyl, N,N-diethylglycine sodium, 2-(dimethylamino) ethylacetate, N-methylimimino diacetic acid, N,N-dimethylamino ethylacrylate, N,N-diethylamino ethylmethacrylate, N,N-diisopropylamino ethylmethacrylate, N,N-dibutylamino ethylmethacrylate, N,N-dibenzylamino ethylmethacrylate, 3-dimethylamino propionitrile, tris (2-cyanoethyl) amine, N,N-dimethyl allylamine, N,N-diethyl allylamine and triallylamine.

The dental photocurable composition of the present disclosure contains (D-1) aliphatic tertiary amine compound represented by formula (1) as the (D) photopolymerization accelerator.

[Chemical formula 2]

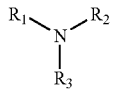
[Formula (1)]

In formula, $R_1$ represents a substituent consisting of three or more carbons having an electron-withdrawing group at α-carbon and/or β-carbon of an amine starting from N, $R_2$ represents a substituent consisting of three or more carbons which may have an electron-withdrawing group, $R_3$ represents a substituent consisting of one or more carbons which may have an electron-withdrawing group, and α-carbon of N in the formula (1) is not an electron-withdrawing group.

The electron-withdrawing group in $R_1$ may be a substituent selected from a functional group selected from the group consisting of a hydroxyl group, a carboxyl group, a vinyl group, an aryl group and a halogen, and, an organic group which is bonded via an ether bond, an ester bond, a urethane bond or a urea bond and may have —OH group, —O-group, —C(O)-group, —S-group, —NH—C(O)—NH-group, —C(O)—O-group, —O—C(O)-group, —OC(O)—NH-group, —NH—C(O)—O-group, an aromatic hydrocarbon group, or a polymerizable functional group capable of radical polymerization.

Conventionally, an aliphatic tertiary amine such as dimethylaminoethyl methacrylate or triethanolamine have been compounded to the dental photocurable composition for the purpose of promoting photopolymerization, improving solubility and improving storage stability. However, when the above described conventional aliphatic tertiary amine and the (E1) hydrophobized silica fine particle having an average diameter of primary particle of 1 to 40 nm are coexisted in the composition, there is a tendency that the rheological property exhibited by the hydrophobized silica fine particle is deactivated in the case of storing the composition in an incubator set at 50° C. for one month or more which corresponds to long-term storage or long-term storage equivalent. On the other hand, when an aromatic tertiary amine compound having an electron-withdrawing group at p-position such as N,N-bis (2-hydroxyethyl)-p-toluidine, N,N-bis (2-hydroxypropyl)-p-toluidine and ethyl 4-(dimethylamino) benzoate or an aromatic tertiary amine compound having a dihydroxyalkyl group is used in combination, rheological property is not deactivated, but there is a case that an aromatic tertiary amine cause deterioration of sensitivity to light or deterioration of color stability after irradiation. In this case, improvement of the color stability after irradiation can be expected by compounding an ultraviolet absorber. However, when a large amount of the aromatic amine compound is compounded to ensure physical property by only the aromatic amine compound, it is necessary to increase the compounding amount of the ultraviolet absorber for improving the color stability after irradiation. When a large amount of an ultraviolet absorber is compounded, there is a case that the mechanical property deteriorates. Therefore, there is a case that it is not preferable to compounding only an aromatic amine compound as a photopolymerization accelerator. In order to improve these problems, attention has been paid on the (D1) aliphatic tertiary amine compound represented by formula (1). By using the (D1) aliphatic tertiary amine compound represented by formula (1) in the dental photocurable composition, the rheological property can be maintained even when storing for a long period of time, expressing sufficient mechanical strength for use in a dental application succeeded. In addition, there has been a tendency to exhibit color stability after irradiation suitable for a dental application. More preferably, it has been found that the (D1) aliphatic tertiary amine compound represented by formula (1) exhibits high mechanical strength in the case of containing the (B) photosensitizer, especially further containing the (C) photoacid generator in the dental photocurable composition, and have completed the present disclosure.

In the present disclosure, rheological property is evaluated using flowability. The flowability means the distance moved by the dental photocurable composition in 1 minute after vertically fixing a glass slide so as to make an angle at 90° to the horizontal plane in 5 seconds after adhering 0.05 g of the dental photocurable composition in a lump state on the horizontally placed slide glass plane.

As the dental photocurable composition, those having various fluidities are used. For example, there is various composition including a composition with a high flowability of 10 mm is particularly useful in the case of being used in a portion having a complex shape such as a convexoconcave portion and constriction portion, a composition with a flowability of 0 mm is particularly useful for a portion where morphological maintenance is required such as the formation of septum, and a composition with a flowability of 5 mm is used for the case of not specialized for specific use. A change in flowability after long-term storage means that the good operability of the dental photocurable composition is lost.

In the (D1) aliphatic tertiary amine compound represented by formula (1), $R_1$ represents a substituent consisting of three or more carbons having an electron-withdrawing group at α-carbon and/or β-carbon of an amine starting from N, $R_2$ represents a substituent consisting of three or more carbons which may have an electron-withdrawing group, $R_3$ represents a substituent consisting of one or more carbons which may have an electron-withdrawing group. Here, $R_2$ and $R_3$ may be a carbon alicyclic compound or a complex alicyclic compound in which three or more carbons are cyclically bonded. For the meaning of α-position and/or β-position starting from N, the carbon bonded to N is the α-position carbon and the carbon bonded to the α-position carbon is the β-position carbon. The number of the carbon in the substituent consisting of three or more carbons includes the carbon contained in the electron-withdrawing functional group. Further, N represented by the formula (1) does not bond with an electron-withdrawing group without passing through a hydrocarbon group. That is, the α-position carbon itself is not an atom that constitutes an electron-withdrawing group, and the (D1) aliphatic tertiary amine compound represented by formula (1) is bonded with a functional group having electron-withdrawing property at the α-position carbon and/or the β-position carbon.

The electron-withdrawing group refers a substituent that easily attracts an electron from the bonded atom side. Examples of the electron-withdrawing group include a hydroxyl group, a thiol group, a nitro group, a carbonyl group, a carboxyl group, a sulfonyl group, a cyano group, an aryl group, an amino group, a halogen, and an organic group bonded via an unsaturated bond such as a vinyl group and a propargyl group, an ether bond, an ester bond, a urethane bond or a urea bond.

Among the electron-withdrawing groups in the formula (1), the electron-withdrawing group of the α-carbon and/or β-carbon of $R_1$ may be a functional group selected from the group consisting of a hydroxyl group, a carboxyl group, a vinyl group, an aryl group and a halogen, and, an organic group which is bonded via an ether bond, an ester bond, a urethane bond or a urea bond. This organic group may have —OH group, —O-group, —C(O)-group, —S-group, —NH—C(O)—NH-group, —C(O)—O-group, —O—C (O)-group, —OC(O)—NH-group, —NH—C(O)—O-group, an aromatic hydrocarbon group, or a polymerizable functional group capable of radical polymerization. Preferable is a hydroxyl group, a carboxyl group, an aryl group and an organic group having an ether bond, an ester bond, a urethane bond or a urea bond. More preferable is an aryl group, a carboxyl group and an organic group having an ester bond or a urethane bond because steric hindrance is large or high electron attraction is expected. Further preferable is a tertiary aliphatic amine compound in which the amino group is disubstituted or more with an aryl group which may have a substituent.

When $R_2$ and $R_3$ have an electron-withdrawing group, the electron-withdrawing group may be a functional group selected from the group consisting of a hydroxyl group, a carboxyl group, a vinyl group, an aryl group and a halogen, and, an organic group which is bonded via an ether bond, an ester bond, a urethane bond or a urea bond. This organic group may have —OH group, —O-group, —C(O)-group, —S-group, —NH—C(O)—NH— group, —C(O)—O-group, —O—C(O)-group, —OC(O)—NH-group, —NH—C(O)—O-group, an aromatic hydrocarbon group, or a polymerizable functional group capable of radical polymerization. Preferable is a hydroxyl group, a carboxyl group, an aryl group and an organic group having an ether bond, an ester bond, a urethane bond or a urea bond. More preferable is an aryl group, a carboxyl group and an organic group having an ester bond or a urethane bond because steric hindrance is large or high electron withdrawing is expected. Furthermore, preferable is a tertiary aliphatic amine compound in which the amino group is disubstituted or more with an aryl group which may have a substituent.

In the formula (1), an aliphatic tertiary amine compound in which $R_1$ and $R_2$ have an aliphatic substituent consisting of three or more carbons having an electron-withdrawing group at α-carbon and/or β-carbon is preferable. In this case, a high level of maintenance of rheological property can be expected in the case of storing the photocurable dental composition. Furthermore, an aliphatic tertiary amine compound in which the amino group is disubstituted or more with an aryl group which may have a substituent, that is, an aliphatic tertiary amine compound having an aryl group which may have a substituent at α-carbon and/or β-carbon is preferable. Specific examples include tribenzylamine, dibenzylglycine ester compound and dibenzylaminoalkyl (meth) acrylate. A compound having such a structure is expected to have an effect not only of stabilizing fluidity particularly but also of exhibit high mechanical strength in the case of compounding in the dental photocurable composition containing the (E1) hydrophobized silica fine particle having an average diameter of primary particle of 1 to 40 nm.

Specific examples of the (D1) aliphatic tertiary amine compound represented by formula (1) include triisopropanolamine, 2-(dibutylamino)-1-phenyl-1-propanol, 1-[(3,3-diphenylpropyl) (methyl) amino]-2-methyl-2-propanol, 3,3', 3"-nitrilotripropionic acid, N-benzyl-3,3'-iminodipropionic acid, 1-benzhydrill azetidine-3-carboxylic acid, 1-benzyl-3-pyrrolidone, 1-(2-phenylethyl)-4-piperidone, 1-benzylpiperidin, 1-phenyl-2-(1-pyrrolidinyl) propan-1-ol, 2-[hydroxy (diphenyl) methyl]-1-methylpyrrolidin, N,N,N',N'-tetrakis (2-hydroxypropyl) ethylenediamine, N,N,N',N",N"-pentakis (2-hydroxypropyl) diethylenetriamine, 2-piperidino-1,1,2-triphenylethanol, 2-[benzyl (methyl) amino]-1-phenylethanol, 2-(dibenzylamino)-3-phenyl-1-propanol, 2,6-bis [2-(hydroxy diphenylmethyl)-1-pyrrolidinyl-methyl]-4-methylphenol, 2-benzyl-1,2,3,4-tetrahydro isoquinolin-ε-carboxylic acid, 2-benzyl-1,2,3,4-tetrahydro isoquinolin-3-carboxylic acid, 2-(dibenzylamino) propionaldehyde, 3-(dibenzylamino)-1-propanol, 2-(dibenzylamino)-1-propanol, 2-(N,N-dibenzylamino)-3-methylbutanol, 1-[(dibenzylamino) methyl]-2-naphthanol, 2-(dibenzylamino)-4-methyl-1-pentanol, 4-dibenzylamino-cyclohexanone, 3-dibenzylamino-2-fluoropropionic acid benzyl ester, N,N-dibenzyl-1,4-dioxaspiro [4.5]decane-8-amine, N,N-dipropyl-L-alanine, N,N-dibenzyl-2-aminoethanol, N,N-dibenzyl glycineethyl, tribenzylamine, triallylamine, 1,1'-(methylimino) dipropane-2-ol, 1-(benzyl (2-methylallyl) amino)-2-methylpropan-2-ol, 2-piperidino-1,1,2-triphenylethanol, N,N-dibenzylaminoethanol, N,N-dibenzylaminopropanol and 3-(N,N-dibenzylamino) propyltriethoxysilane. In addition, examples include a transesterification product of tertiary amine compound containing OH group such as N,N-dibenzyl aminoethanol, N,N-dibenzyl aminopropanol, N,N-dibutyl ethanolamine, N,N-diisopropyl aminoethanol, N-methyldiethanolamine, N-ethyldiethanolamine, N-butyldiethanolamine and N-tert-butyl diethanolamine and ester compound containing (meth) acrylic acid ester such as methyl methacrylate and butyl methacrylate, an urethane compound synthesized by reaction of tertiary amine compound containing OH group and compound having isocyanate such as 2-isocyanatoethyl (meth) acrylate and 1,1-(bisacryloyloxymethyl) ethylisocyanate, a transesterification product of an amine compound having a carboxyl group or ester bond such as 3,3',3"-nitrillo tripropionic acid, N-benzyl-3,3'-iminodipropionic acid, N-methylimino diacetic acid, N-(2-hydroxyethyl) iminodiacetic acid, N-(2-carboxyethyl) iminodiacetic acid, N, N-dipropyl-L-alanine and N,N-dibenzylglycine and a compound having an OH group such as an alcohol and 2-hydroxyethyl methacrylate, and an urea compound synthesized by a reaction of a secondary amine such as diisopropylamine and dibenzylamine and a compound having an isocyanate such as 2-isocyanatoethyl (meth) acrylate or 1,1-(bisacryloyl oxymethyl) ethyl isocyanate. Among these, dibenzylaminoethyl methacrylate and dibenzylaminopropyl methacrylate which are transesterification products of a tertiary amine compound having OH group such as dibenzylaminoethanol and dibenzylaminopropanol, and an ester compound having a polymerizable group including (meth) acrylic acid ester, an urethane compound synthesized by reaction with compound having isocyanate such as 2-isocyanatoethyl (meth) acrylate and 1,1-(bisacryloyl oxymethyl) ethylisocyanate, N,N-dibenzylglycine ester compound, N-alkyldibenzylamines such as tribenzylamine and N-methyldibenzylamine are preferable.

The compounding amount of the (D1) aliphatic tertiary amine compound represented by formula (1) is preferably 0.1 parts by mass or more and 10 parts by mass or less, more preferably 0.5 parts by mass or more and 5 parts by mass or less, with respect to 100 parts by mass of the (A) polymerizable monomer contained in the dental photocurable composition. When the compounding amount of the (D1) aliphatic tertiary amine compound represented by formula (1) is less than 0.1 parts by mass, the polymerization promoting ability is poor and the curing tends to be insufficient. When the compounding amount is more than 10 parts by mass, although sufficient curability is exhibited, there is a case that the sensitivity to light is shortened, and discoloration of the cured body increases.

The type of the (D) photopolymerization accelerator may be appropriately selected according to the type and the compounding amount of other components to be combined. In addition, the (D) photopolymerization accelerator may be used not only singly but also in combinations of two or more.

The compounding amount of the (D) photopolymerization accelerator is preferably 0.1 parts by mass or more and 10 parts by mass or less, more preferably 0.5 parts by mass or more and 5 parts by mass or less, with respect to 100 parts by mass of the total amount of the (A) polymerizable monomer contained in the dental photocurable composition. When the compounding amount of the (D) photopolymerization accelerator is less than 0.1 parts by mass, the polymerization promoting ability is poor and the curing tends to be insufficient. When the compounding amount is more than 10 parts by mass, although sufficient curability is exhibited, there is a case that the sensitivity to light is shortened, and discoloration of the cured body increases.

The dental photocurable of the present disclosure may contain only the (D-1) aliphatic tertiary amine compound represented by formula (1) as the (D) photopolymerization accelerator. The dental photocurable of the present disclosure may contain only the (D-1) aliphatic tertiary amine compound represented by formula (1) which is an aliphatic tertiary amine compound in which $R_1$ and $R_2$ have an aliphatic substituent consisting of three or more carbons having an electron-withdrawing group at α-carbon and/or β-carbon, as the (D) photopolymerization accelerator. The dental photocurable of the present disclosure may contain only the (D-1) aliphatic tertiary amine compound represented by formula (1) which is an aliphatic tertiary amine compound in which $R_1$ and $R_2$ have an aryl group which may have a substituent, at α-carbon and/or β-carbon, as the (D) photopolymerization accelerator.

There is no problem even if these (B) photosensitizers, (C) photoacid generators and (D) photopolymerization accelerators, which are polymerization initiators, are subjected to a secondary treatment such as finely pulverization, adsorption on a carrier and encapsulation in a microcapsule, if necessary. Furthermore, these photo polymerization initiators can be used not only singly but also in combinations of two or more, regardless of the polymerization manner or the polymerization method.

[(E) Filler]

As the (E) filler used in the present disclosure, a known filler commonly used can be used without any limitation.

The type of the (E) filler is not limited as long as it is a known filler, and a filler suitable for the application can be compounded, and it is preferable that a filler such as an inorganic filler, an organic filler, an organic-inorganic composite filler and an ion sustained release glass is compounded. In the dental photocurable composition of the present disclosure, the filler described in the specific example may be used alone, or two or more kinds of fillers may be used in combination.

As the inorganic filler, the chemical composition is not particularly limited, but specific examples include silicon dioxide, alumina, titania, silica-titania, silica-titania-barium oxide, silica-zirconia, silica-alumina, lanthanum glass, borosilicate glass, soda glass, barium glass, strontium glass, glass ceramic, aluminosilicate glass, barium boroaluminosilicate glass, strontium boroaluminosilicate glass, fluoroaluminosilicate glass, calcium fluoroaluminosilicate glass, strontium fluoroaluminosilicate glass, barium fluoroaluminosilicate glass, strontium calcium fluoroaluminosilicate glass and the like. Particularly, barium fluoroaluminosilicate glass, strontium fluoroaluminosilicate glass, fluoroaluminosilicate glass and the like, which are used in dental glass ionomer cement, resin reinforced glass ionomer cement and resin cement and the like, can also be suitably used. The fluoroaluminosilicate glass as used herein has a basic structure of silicon oxide and aluminum oxide and contains an alkali metal for introducing non-crosslinked oxygen. The fluoroaluminosilicate glass further has an alkaline earth metal including strontium and fluorine as modified/coordinated ions. The fluoroaluminosilicate glass may be also a composition in which a lanthanoid series element is incorporated into the skeleton in order to impart further radiopacity. This lanthanoid series element also participates in the composition as a modified/coordinated ion.

Specific examples of the organic filler include polymers such as polymethyl methacrylate, polyethyl methacrylate, methyl methacrylate-ethyl methacrylate copolymer, ethyl methacrylate-butyl methacrylate copolymer, methyl methacrylate-trimethylolpropane methacrylate copolymer, polyvinylchloride, polystyrene, chlorinated polyethylene, nylon, polysulfone, polyethersulfone and polycarbonate.

Specific examples of the organic/inorganic composite filler include one obtained by covering the surface of a filler with a polymerizable monomer by polymerization, one obtained by mixing a filler and a polymerization monomer and polymerizing the monomer and thereafter grinding the resultant to a proper particle size, one obtained by dispersing a filler in a polymerizable monomer in advance for emulsion polymerization or suspension polymerization, one obtained by spray-drying a polymerizable monomer and a solvent which are dispersed with a filler in advance and polymerizing, and one obtained by spray-drying a solvent which is dispersed with a filler in advance, impregnating a polymerizable monomer and polymerizing, but are not limited thereto at all.

The feature of the ion sustained release glass is that at least one of fluorine ion, strontium ion, borate ion and aluminum ion is sustained release. Among these ions, it is preferable that a plurality of these ions are released at the same time.

As the ion sustained release glass used in the present disclosure, any ion sustained release glass can be used without any limitation as long as such ion sustained release glass includes one or more kinds of glass skeleton forming elements which form a glass skeleton, and one or more kinds of glass modifying elements which modify the glass skeleton. These ion sustained release glasses may be used alone or in combination of two or more thereof. Further, in the present disclosure, glass amphoteric elements that play a role of either a glass skeleton forming element or a glass modifying element depending on the glass composition are included within a category of a glass skeleton forming element. Specific examples of the glass skeleton forming element contained in the ion sustained release glass, include silica, aluminum, boron and phosphorus, and these can be used not only singly but also in combinations of a plurality thereof. Specific examples of the glass modifying element include halogen elements such as fluorine, bromine and iodine, alkali metal elements such as sodium and lithium, and alkali earth metal elements such as calcium and strontium, and these can be used not only singly but also in combinations of a plurality thereof. Among them, a glass composition including silica, aluminum or boron as the glass skeleton forming element and including fluorine, sodium or strontium as the glass modifying element is preferable, and specific examples include a silica glass, a fluoroaluminosilicate glass, a fluoroborosilicate glass and a fluoroalumino borosilicate glass containing strontium or sodium. Furthermore, from the viewpoint of sustainably releasing fluorine ion, strontium ion, borate ion or aluminum ion, a fluoroalumino borosilicate glass containing strontium is more preferable. Example of the glass composition range thereof is as follows: $SiO_2$: 15 to 35% by mass, $Al_2O_3$: 15 to 30% by mass, $B_2O_3$: 5 to 20% by mass, SrO: 20 to 45% by mass, F: 5 to 15% by mass, and $Na_2O$: 0 to 10% by mass. The glass composition can be confirmed by using an instrumental analysis such as an elementary analysis, Raman spectrum, and fluorescence X-ray analysis, and there is no problem as long as the actual measurement by any analysis methods matches to these composition ranges.

There is no restriction in particular in a preparation method for these glasses, and it can be prepared by a preparation method such as melting method or sol-gel method. Among them, a preparation method of a melting method using a melting furnace is preferable from the viewpoint of an easy design for the glass composition, including raw material selection. The ion sustained release glass used in the present disclosure has an amorphous structure, but there is no problem even if it contains a partially crystalline structure, and further, there is no problem even if it is a mixture of a glass having an amorphous structure and a glass having a crystal structure. Whether the structure of the glass is an amorphous structure or not can be determined using an analytical instrument such as X-ray diffraction analysis and a transmission electron microscope. Among them, it is preferable that the ion sustained-release glass used for the present disclosure has an amorphous structure having a homogeneous structure since it sustained-releases various ions based on an equilibrium relation with ion concentration in the external environments.

Further, in order to enhance ion sustained release property of the ion sustained release glass, it is preferable embodiment to functionalize the glass surface by a surface treatment, thereby improving the ion sustained-release property. Specific examples of a surface treatment material used in the surface treatment include a surfactant, a fatty acid, an organic acid, an inorganic acid, a monomer, a polymer, various coupling materials, a silane compound, a metal alkoxide compound, and a partially condensed product thereof. Among these surface treatment materials, it is preferable to perform composite surface treatment using an acidic polymer and a silane compound.

The composite surface treatment is a method for surface treatment by using an acidic polymer after coating the surface of the ion sustained release glass with a silane compound. Specific example is described in the following. A silane compound represented by the formula (3) is mixed in an aqueous dispersion containing an ion sustained release glass finely pulverized to a desired average particle diameter (D50) by pulverization or the like. The mixture is hydrolyzed or partially hydrolyzed in the system to prepare a silanol compound. Then the silanol compound is condensed to form a polysiloxane, and then the surface of the ion sustained release glass is coated with the polysiloxane to obtain a polysiloxane coated ion sustained release glass.

[Chemical Formula 3]

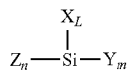

[Formula (3)]

(in the formula, Z is $RO^-$, X is halogen, Y is OH—, R is an organic group whose carbon number is less than or equal to 8, and n, m, and L are each an integer from 0 to 4 where n+m+L=4)

Specific Examples of the silane compound represented by the formula (3) include tetramethoxysilane, tetraethoxysilane, tetrapropoxysilane, tetraallyloxysilane, tetrabutoxysilane, tetrakis (2-ethylhexyloxy) silane, trimethoxychlorosilane, triethoxychlorosilane, triisopropoxychlorosilane, trimethoxyhydroxysilane, diethoxydichlorosilane, tetraphenoxysilane, tetrachlorosilane and silicon hydroxide (silicon oxide hydrate), more preferable include tetramethoxysilane and tetraethoxysilane.

A low condensed product of the silane compound represented by the formula (3) is more preferable. Examples include a low condensed silane compound obtained by partial hydrolysis and condensation of tetramethoxysilane and tetraethoxysilane. These compounds can be used singly or in combination. An organosilane compound can also be added in the polysiloxane treatment as a part of the silane compound represented by the formula (3).

The polysiloxane coated ion sustained release glass obtained in the above step, can be obtained as a most preferable ion sustained release glass by performing an acidic polymer treatment which reacts with acidic polymer. The acidic polymer treatment can be conducted by using an equipment commonly used in the art as long as the equipment is a dry fluid type stirring machine, and examples include a Henschel mixer, a super mixer and a high-speed mixer. The reaction of the ion sustained release glass formed with the polysiloxane film and an acidic polymer can be conducted by contacting an acidic polymer solution by impregnating, spraying or the like. As an example, it is only necessary to perform a dry fluid of the polysiloxane coated ion sustained release glass, dispersing the acid polymer solution from above in the flow state, and sufficiently stirring. The method for dispersing the acidic polymer solution is not particularly limited, and a dropping or spraying method that can uniformly disperse is more preferable. The reaction is preferably conducted around room temperature, and when the temperature increases, there is a case that the reaction of an acid reactive element and the acidic polymer is fast, and thereby formation of an acidic polymer layer is not uniform.

It is preferable to remove the water content in the cement reaction phase by performing a heat treatment after the reaction. If water content remains in the cement reaction phase, it is disadvantageous in terms of strength, but since the filler of the present disclosure is covered and strengthened by the coupling agent condensate film, the decrease in mechanical strength is suppressed. The heat treatment method after the acid polymer treatment is not particularly limited, and can be performed by a known general method. As the equipment used for the heat treatment, a box-type hot air dryer or the like, a rotary heat treatment device capable of uniform heating and the like are preferable. The heat treatment temperature is in the range from room temperature to 200° C., more preferably in the range from 40 to 150° C. When the temperature is lower than this range, there is a risk that the removal of the aqueous medium is insufficient, and when the temperature is higher than this range, there is a risk that the organic layer of the acidic polymer is decomposed or discolored. Since the heat treatment period depends on the capacity of the dryer and the like, there is no problem as long as the aqueous medium can be sufficiently removed. After a heat treatment, a heat-treated product can be easily deagglomerated by application of a shear force or an impact force, and the deagglomerating method can be performed by, for example, the equipment used in the above reaction.

A solvent used for preparing the acid polymer solution used for the reaction may be solvent which dissolves the acid polymer without any problems. Examples of the solvent include water, ethanol, and acetone. Among them, water is particularly preferable. When water is used, an acid group of the acid polymer dissociates and reacts uniformly with the polysiloxane-coated ion sustained release glass. The weight average molecular weight of the polymer dissolved in the acid polymer solution is in the range of 2000 to 50000, and preferably in the range of 5000 to 40000. In the case of treating with the acidic polymer having a weight average molecular weight of less than 2000, there is a tendency that an acidic polymer reaction phase is not formed in the ion sustained release glass, and as a result, the ion sustained release property is low. On the other hand, in the case of treating with an acidic polymer having a weight average molecular weight of more than 50000, the viscosity of the acidic polymer solution becomes high, and therefore it may be difficult to uniformly treat the polysiloxane coated ion sustained release glass. The concentration of the acidic polymer in the acidic polymer solution is preferably in the range from 3 to 25% by mass, more preferably in the range from 8 to 20% by mass. When the concentration of the acidic polymer is less than 3% by mass, the above described acidic polymer reaction phase is brittle and therefore the effect of improving the sustained release of ions cannot be obtained. When the concentration of the acidic polymer is more than 25% by mass, the polysiloxane layer (porous) is difficult to diffuse in a uniform state, a homogeneous acidic polymer reaction phase is not obtained, and the reaction occurs immediately after contact with the polysiloxane coated ion sustained release glass, and therefore there is a problem that strongly reacted agglomerates generates. The addition amount of the acidic polymer solution to the polysiloxane coated ion sustained release glass is preferably in the range from 6 to 40% by mass, more preferably 10 to 30% by mass. Converting in this addition amount, an optimal amount of the acid polymer with respect to the polysiloxane coated ion sustained release glass is in the range of 1 to 7% by mass, and an optimal amount of water is in the range of 10 to 25% by mass.

As the acid polymer that can be used in order to form the acid polymer reaction phase on the surface of the polysiloxane coated ion sustained release glass by the method described above, any copolymers or homopolymers as long as the copolymer or homopolymer of a polymerizable monomer having an acid group such as a phosphoric acid residue, a pyrophosphoric acid residue, a thiophosphoric acid residue, a carboxylic acid residue, or a sulfonic acid residue can be used without any problem. Specific examples of these polymerizable monomers include acrylic acid, methacrylic acid, 2-chloroacrylic acid, 3-chloroacrylic acid, aconitic acid, mesaconic acid, maleic acid, itaconic acid, fumaric acid, glutaconic acid, citraconic acid, 4-(meta) acryloyloxy ethoxycarbonyl phthalic acid, 4-(meta) acryloyloxy ethoxycarbonyl phthalic anhydride, 5-(meta) acryloylamino pentylcarboxylic acid, 11-(meth) acryloyloxy-1,1-undecane dicarboxylic acid, 2-(meta) acryloyloxyethyl dihydrogen phosphate, 10-(meta) acryloyloxydecyl dihydrogen phosphate, 20-(meta) acryloyloxyeicosil dihydrogen phosphate, 1,3-di (meth) acryloyloxypropyl-2-dihydrogen phosphate, 2-(meta) acryloyloxyethyl phenyl phosphate, 2-(meta) acryloyloxyethyl-2'-bromoethyl phosphate, (meta) acryloyloxy-ethyl phenylphosphonate, [2-(meth) acryloyloxyethyl] pyrophosphate, 2-(meta) acryloyloxyethyl dihydrogen dithiophosphate and 10-(meta) acryloyloxydecyl dihydrogen thiophosphate. Among polymers which are (co) polymer of these polymerizable monomers, a homopolymer or a copolymer of α-β unsaturated carboxylic acid that is relatively slow in acid-base reaction with an acid reactive element contained in the polysiloxane coated ion sustained release glass is preferable, and specific examples include an acrylic acid polymer, an acrylic acid-maleic acid copolymer, and an acrylic acid-itaconic acid copolymer.

The above described (E) filler can be treated with a surface treatment material represented by a silane coupling material in order to improve the affinity to the polymerizable monomer, the dispersability in the polymerizable monomer, and the mechanical strength and water resistance of the cured product. The surface treatment material and the surface treatment method are not particularly limited, and known methods such as a method of spraying the surface treatment material while stirring the powdery filler, a method of dispersing and mixing the filler and the surface treatment material in a solvent, and a method of supplying a vapor or gaseous silane coupling material to the filler surface, can be adopted without limitation. As a silane coupling material used for surface treatment of the filler, methyltrimethoxysilane, methyltriethoxysilane, methyltrichlorosilane, dimethyldichlorosilane, trimethylchlorosilane, vinyltrichlorosilane, vinyltriethoxysilane, vinyltris (2-methoxyethoxy) silane, 3-methacryloyloxypropyl trimethoxysilane, 3-chloropropyl trimethoxysilane, 3-glycidoxypropyl trimethoxysilane, 3-(meth) acryloxypropyl trimethoxysilane, 8-(meth) acryloxyoctyl trimethoxysilane, 11-(meth) acryloxiundecyl trimethoxysilane, hexamethyldisilazane and the like are preferable. In addition to the silane coupling material, surface treatment of the filler can be performed by a method using a titanate coupling material or an aluminate coupling material. The treatment amount of the surface treatment material in the filler is preferably 0.01 to 30 parts by mass, more preferably 0.5 to 20 parts by mass with respect to 100 parts by mass of the filler before treatment.

The shape of the (E) filler is not particularly limited, and any shape of the filler such as a spherical shape, a needle shape, a plate shape, a crushed shape or a scale shape can be used. The average particle diameter of the filler is preferably 0.01 μm to 50 μm, more preferably 0.01 μm to 30 μm, still more preferably 0.05 μm to 20 μm, and more preferably 0.05 μm to 10 μm.

The dental photocurable composition of the present disclosure contains (E1) hydrophobic silica fine particle having an average particle diameter of the primary particles of 1 to 40 nm. The (E1) hydrophobic silica fine particle having an average particle diameter of the primary particles of 1 to 40 nm is used to impart thixotropic property among rheological property to a dental photocurable composition. The primary particle diameter indicates the diameter of one particle (primary particle) constituting the powder. In the present disclosure, the average particle diameter may be, for example, an average particle diameter calculated based on a volume-based grain size distribution measured by a laser diffraction type particle size distribution measuring device or the like, and may be measured by, for example, a laser diffraction type grain size measuring apparatus (Microtrac MT3300EXII: NIKKISO Co., Ltd.). In addition, the primary particle diameter can be measured by dynamic light scattering particle size measurement and can be measured by using electron micrographs for the case that primary particles are strongly aggregated to form secondary particles.

The (E1) hydrophobized silica fine particle having an average diameter of primary particle of 1 to 40 nm is hydrophobic silica fine particle hydrophobized by surface treatment with a silane coupling agent and/or a modified silicone oil.

Specific Examples of a method for hydrophobizing a hydrophobized silica fine particle include surface treatment with a modified silicone oil such as dimethylsilicone oil and/or surface treatment with a silane coupling material which has an alkylsilyl group and may have a trimethylsilyl group, a dimethylsilyl group, a methylsilyl group or a (meth) acryloyl group having an alkyl chain having 3 or more and 18 or less carbon atoms. It is preferable that the silane coupling agent is hydrophobized via a covalent bond to a fine silica particle.

Specific examples of a modified silicone oil and a silane coupling agent material include alkoxysilanes such as polydimethylsiloxane, hexamethyl disilazane, dimethylpolysiloxane, methylchlorosilane, alkyltrialkoxysilane, dialkyl dialkoxysilane, octadecylalkoxysilane and octylalkoxysilane, and (meth)acryloylalkyl alkoxysilanes such as 3-methacryloylpropyl trimethoxysilane and 8-methacryloyloctyl trimethoxysilane.

In order to further improve rheological property, a silica fine particle may be hydrophobized by multiple methods. For example, after treatment with a silane coupling agent and/or a modified silicone oil, or at the same time, treatment with a surface treatment agent may be performed.

Examples of the (E1) hydrophobized silica fine particle having an average diameter of primary particle of 1 to 40 nm include a dry silica, a silica aerogel, and a wet silica, and a dry silica is preferable.

Among the above described hydrophobized silica fine particles, examples of the dry silica is manufactured and marketed under the trade name of Aerosil by Nippon Aerosil Co., Ltd. Specific examples include a silica fine powder of which surface is subjected to hydrophobizing treatment such as Aerosil R972, Aerosil R974, Aerosil R976, Aerosil R976S, Aerosil R202, Aerosil R812, Aerosil R812S, Aerosil R805, Aerosil R104, Aerosil R106, Aerosil RY200, Aerosil RX200, Aerosil R711, Aerosil RY200S, Aerosil RA200H, Aerosil R8200 and Aerosil RA200HS may be used.

It is preferable that the compounding amount of the (E1) hydrophobized silica fine particle having an average diameter of primary particle of 1 to 40 nm, with respect to 100 parts by mass of the (A) polymerizable monomer, is within a range of 0.5 to 30 parts by mass, preferably 1 to 20 parts by mass. When the compounding amount is less than 0.5 parts by mass with respect to 100 parts by mass of the (A) polymerizable monomer, there is a case that expression of rheological property in the dental photocurable composition is not expected, and when the compounding amount exceeds 30 parts by mass, there is a case that the photocurable dental composition is significantly thickened, resulting in poor operational feeling.

It is preferable that the dental photocurable composition further comprises (E2) inorganic filler having an average diameter of primary particle of 0.1 to 10 µm as the (E) filler, and a total amount of the (E2) inorganic filler and the (E1) hydrophobized silica fine particle is 100 to 400 parts by mass with respect to 100 parts by mass of the (A) polymerizable monomer. The (E2) inorganic filler has a larger average particle diameter size than the (E1) hydrophobized silica fine particle. In general, when a large amount of particles having an average particle diameter of nano-order is compounded, the viscosity increases significantly to deteriorate operability, therefore the compounding amount is limited. On the other hand, since a higher strength is required in the photocurable dental composition depending on the application, the compounding amount of the filler is preferably large within a range that does not affect the operability. In the present disclosure, by compounding the (E1) hydrophobized silica fine particles having an average diameter of primary particles of 1 to 40 nm and the (E2) inorganic filler having an average diameter of primary particles of 0.1 to 10 µm, it is expected that the dental photocurable composition has moderate operability and high mechanical property. In addition, the (E2) inorganic filler can be compounded for purposes other than increasing strength, such as imparting X-ray contrast, imparting ion release property, imparting color tone conformity, adjusting color tone toning, improving adhesive property and improving operability.

It is preferable that the compounding amount of (E) filler in the present disclosure, with respect to 100 parts by mass of the total amount of the (A) polymerizable monomer, is 400 parts by mass or less. When the compounding amount of the (E) filler exceeds 400 parts by mass, there is a case that the photocurable dental composition does not have fluidity to decrease operability.

In the dental photocurable composition of the present disclosure, it is preferable that the difference between a flowability of the dental photocurable composition after standing in a thermostatic chamber set at 50° C. for one month after preparation and a flowability of the dental photocurable composition after preparation is 3.0 mm or less. Since the dental photocurable compositions has various fluidities depending on the application, a change in fluidity after long-term storage means a decrease in operability because it is difficult to use appropriately.

In the dental photocurable composition of the present disclosure, it is preferable that both the flowability of the dental photocurable composition after standing in a thermostatic chamber set at 50° C. for one month after preparation and the flowability of the dental photocurable composition after preparation are 3.0 mm or less. A dental photocurable composition having a fluidity of 3.0 mm or less is less likely to drip, therefore it can be applied to the site intended by the user. On the other hand, when the fluidity changes after long-term storage, the user is likely to feel a decrease in operability, therefore high property stability is required. Since the dental photocurable composition of the present disclosure can maintain its fluidity over a long period of time, it is particularly suitable for application to a dental photocurable composition having a fluidity of 3.0 mm or less.

The dental photocurable composition of the present disclosure may contain a chemical polymerization initiator. Specific examples of an organic peroxide as chemical polymerization initiator include diacyl peroxides, peroxy esters, dialkyl peroxides, peroxy ketals, ketone peroxides, peroxy dicarbonates, and hydro peroxides. Specific examples of diacyl peroxides include acetyl peroxide, isobutyryl peroxide, benzoyl peroxide, decanoyyl peroxide, 3,5,5-trimethylhexanoyl peroxide, 2,4-dichlorobenzoyl peroxide, and lauroyl peroxide and the like. Specific examples of peroxyesters include α-cumylperoxy neodecanoate, t-butylperoxy neodecanoate, t-butylperoxy pivalate, 2,2,4-trimethylpentyl peroxy-2-ethyl hexanoate, t-amylperoxy-2-ethylhexanoate, t-butylperoxy-2-ethylhexanoate, di-t-butylperoxy isophthalate, di-t-butylperoxy hexahydro terephthalate, t-butylperoxy-3,3,5-trimethyl hexanoate, t-butylperoxy acetate, t-butylperoxy benzoate and t-butylperoxy maleric acid. Specific examples of dialkyl peroxides include di-t-butyl peroxide, dicumyl peroxide, t-butylcumyl peroxide, 2,5-dimethyl-2,5-di (t-butylperoxy) hexane, 1,3-bis (t-butylperoxy isopropyl) benzene, 2,5-dimethyl-2,5-di (t-butylperoxy)-3-hexyne and the like. Specific examples of peroxyketals include 1,1-di (t-butylperoxy) cyclohexane, 2,2-di (t-butylperoxy) butane, and n-butyl-4,4-(t-butylperoxy) parerate, 1,1-di (t-amylperoxy) cyclohexane and the like. Specific examples of ketone peroxides include methyl ethyl ketone peroxide, methyl isobutyl ketone peroxide, methyl cyclohexanone peroxide, cyclohexanone peroxide and the like. Specific examples of peroxydicarbonates include di-3-methoxyperoxy dicarbonate, di-2-ethylhexylperoxy dicarbonate, bis (4-t-butylcyclohexyl) peroxy dicarbonate, diisopropylperoxy dicarbonate, di-n-propylperoxy dicarbonate, di-2-ethoxyethylperoxy dicarbonate, diallylperoxy dicarbonate and the like. Specific examples of hydroperoxides include 2,5-dimethyl hexane-2,5-dihydroperoxide, diisopropylbenzene hydroperoxide, cumene hydroperoxide, t-butyl hydroperoxide and 1,1,3,3-tetramethyl butylhydroperoxide.

In the dental photocurable composition of the preset disclosure, the above-described organic peroxides may be used alone, or two or more kinds of organic peroxides may be used in combination. Among these organic peroxides, benzoyl peroxide and cumene hydroperoxide, 1,1,3,3-tetramethylbutyl hydroperoxide and 1,1,3,3-tetramethylbutyl peroxy-2-ethylhexanoate are preferable from the viewpoint of curability.

The compounding amount of the organic peroxide as a chemical polymerization initiator is preferably set to 0.1 to 5 parts by mass, more preferably set to 0.3 to 3 parts by mass with respect to 100 parts by mass of the total amount of the (A) polymerizable monomer from the viewpoint of improving the curability. When the compounding amount of the organic peroxide is more than 5 parts by mass, it may be difficult to ensure sufficient operation time. On the other hand, when the compounding amount of the organic peroxide is less than 0.1 parts by mass, there is a case in which mechanical strength is insufficient.

In the dental photocurable composition of the present disclosure, in order to improve the curability, a chemical polymerization accelerator may further be compounded. Examples of chemical polymerization accelerators include a transition metal compound of the group 4 in the periodic table, a thiourea derivative an aliphatic amine, an aromatic amine, a sulfinic acid and a salt thereof, a borate compound, a sulfur-containing reductive inorganic compound, a nitrogen-containing reductive inorganic compound, a barbituric acid derivative, a triazine compound, a halogen compound and the like. The compounding amount of the chemical polymerization accelerator is preferably 0.01 to 5 parts by mass, more preferably 0.1 to 3 parts by mass, with respect to 100 parts by mass of the total amount of (A) polymerizable monomer.

The transition metal compound of the period 4 in the periodic table as a chemical polymerization accelerator refers to a metal compound of groups 3 to 12 of the period 4 in the periodic table, and specifically, each metal compound of scandium (Sc), titanium (Ti), vanadium (V), manganese (Mn), iron (Fe), cobalt (Co), nickel (Ni), copper (Cu), and zinc (Zn) can be used without any limitation. Although each of the above transition metal element may have a multiple valences, they can be added to the dental photocurable composition of the present disclosure as long as the valence is stable. Examples include Sc (trivalent), Ti (tetravalent), V (trivalent, tetravalent or pentavalent), Cr (divalent, trivalent or hexavalent), Mn (divalent to heptavalent), Fe (divalent or trivalent), Co (divalent or trivalent), Ni (divalent), Cu (monovalent or divalent), Zn (divalent). Specific examples of the transition metal compound include scandium iodide (trivalent) and the like as a scandium compound, titanium chloride (tetravalent), titanium tetraisopropoxide (tetravalent) and the like as titanium compounds, acetylacetone vanadium (trivalent), divanadium tetraoxide (tetravalent), vanadylacetyl acetonate (tetravalent), vanadium stearate oxide (tetravalent), vanadyl oxalate (tetravalent), vanazyl sulfate (tetravalent), oxobis (1-phenyl-1,3-butandionate) vanadium (tetravalent), bis (maltlate) oxovanadium (tetravalent), vanadium pentoxide (pentavalent), sodium metavanadate (pentavalent) and the like as a vanadium compound, manganese acetate (divalent), manganese naphthenate (divalent) and the like as manganese compounds, iron acetate (divalent), iron chloride (divalent), iron acetate (trivalent), iron chloride (trivalent) and the like as an iron compound, cobalt acetate (divalent), cobalt naphthenate (divalent) and the like as a cobalt compound, nickel chloride (divalent) and the like as a nickel compound, copper chloride (monovalent), copper bromide (monovalent), copper chloride (divalent), copper acetate (divalent) and the like as a copper compound, and zinc chloride (divalent), zinc acetate (divalent) and the like as a zinc compound.

Among these, a trivalent or tetravalent vanadium compound and a divalent copper compound are preferable. Among them, because of having higher polymerization accelerating ability, a trivalent or tetravalent vanadium compound is more preferable, and a tetravalent vanadium compound is most preferable. A plurality of kinds of these transition metal compounds in the period 4 in the periodic table may be used in combination, if necessary. The compounding amount of transition metal compound is preferably 0.0001 to 1 parts by mass with respect to 100 parts by mass of the total amount of the (A) polymerizable monomer. When the compounding amount is less than 0.0001 parts by mass, there is a case where the polymerization accelerating effect is insufficient, and when the compounding amount exceeds 1 part by mass, there is a case where it causes discoloration or gelation of the dental photocurable composition and the storage stability is lowered.

Any known thiourea derivatives can be used as the thiourea derivative as the chemical polymerization accelerator without any limitation. Specific examples of the thiourea derivatives include dimethylthiourea, diethylthiourea, tetramethylthiourea, (2-pyridyl) thiourea, N-methylthiourea, ethylenethiourea, N-allylthiourea, N-allyl-N'-(2-hydroxyethyl) thiourea, N-benzylthiourea, 1,3-dicyclohexyl thiourea, N,N'-diphenylthiourea, 1,3-di (p-tolyl) thiourea, 1-methyl-3-phenylthiourea, N-acetylthiourea, N-benzoylthiourea, diphenylthiourea, dicyclohexylthiourea and the like. Among these, (2-pyridyl) thiourea, N-acetylthiourea and N-benzoylthiourea are preferable. A plurality of kinds of these thiourea derivatives can be used in combination, if necessary. The compounding amount of the thiourea derivative is preferably 0.1 to 5 parts by mass with respect to 100 parts by mass of the total amount of the (A) polymerizable monomers. When the compounding amount is less than 0.1 parts by mass, there is a case where the ability as a polymerization accelerator is insufficient, and when the compounding amount exceeds 5 parts by mass, the storage stability may be lowered.

Examples of sulfinic acid and its salt include p-toluene sulfinic acid, sodium p-toluene sulfinate, potassium p-toluene sulfinate, lithium p-toluene sulfinate, calcium p-toluene sulfinate, benzenesulfinic acid, sodium benzene sulfinate, potassium benzene sulfinate, lithium benzenesulfinate, calcium benzenesulfinate, 2,4,6-trimethyl benzenesulfinic acid, sodium 2,4,6-trimethyl benzenesulfinate, potassium 2,4,6-trimethyl benzenesulfinate, lithium 2,4,6-trimethyl benzenesulfinate, calcium 2,4,6-trimethyl benzenesulfinate, 2,4,6-triethyl benzenesulfinic acid, sodium 2,4,6-triethyl benzenesulfinate, potassium 2,4,6-triethyl benzenesulfinate, lithium 2,4,6-triethyl benzenesulfinate, calcium 2,4,6-triethyl benzenesulfinate, 2,4,6-triisopropyl benzenesulfinic acid, sodium 2,4,6-triisopropyl benzenesulfinate, potassium 2,4,6-triisopropylbenzenesulfinate, lithium 2,4,6-triisopropylbenzenesulfinate, calcium 2,4,6-triisopropyl benzenesulfinate and the like. Among them, sodium benzenesulfinate, sodium p-toluenesulfinate, and sodium 2,4,6-triisopropyl benzenesulfinate are particularly preferable.

As the borate compound, specific examples of the borate compound having one aryl group in one molecule include trialkylphenylboron, trialkyl (p-chlorophenyl) boron, trialkyl (p-fluorophenyl) boron, trialkyl (3,5-bistrifluoro methyl) phenyl boron, trialkyl [3,5-bis (1,1,1,3,3,3-hexafluoro-2-methoxy-2-propyl) phenyl] boron, trialkyl (p-nitrophenyl) boron, trialkyl (m-nitrophenyl) boron, trialkyl (p-butylphenyl) boron, trialkyl (m-butylphenyl) boron, trialkyl (p-butyloxyphenyl) boron, trialkyl (m-butyloxyphenyl) boron, trialkyl (p-octyloxyphenyl) boron and trialkyl (m-octyloxyphenyl) boron (the alkyl group is at least one selected from the group consisting of n-butyl group, n-octyl group and n-dodecyl group etc.) and salts thereof (sodium salt, lithium salt, potassium salt, magnesium salt, tetrabutyl ammonium salt, tetramethyl ammonium salt, tetraethyl ammonium salt, methyl pyridinium salt, ethyl pyridinium salt, butyl pyridinium salt, methyl quinolinium salt, ethyl quinolinium salt, butyl quinolinium salt and the like). Specific examples of the borate compound having two aryl groups in one molecule include dialkyl diphenylboron, dialkyl di (p-chlorophenyl) boron, dialkyl di (p-fluorophenyl) boron, dialkyl di (3,5-bistrifluoro methyl) phenyl boron, dialkyl di [3,5-bis (1,1,1,3,3,3-hexafluoro-2-methoxy-2-propyl) phenyl] boron, dialkyl di (p-nitrophenyl) boron, dialkyl di (m-nitrophenyl) boron, dialkyl di (p-butylphenyl) boron, dialkyl di (m-butylphenyl) boron, dialkyl di (p-butyl oxyphenyl) boron, dialkyl di (m-butyl oxyphenyl) boron, dialkyl di (p-octyl oxyphenyl) boron and dialkyl di (m-octyl oxyphenyl) boron (the alkyl group is at least one selected from the group consisting of n-butyl group, n-octyl group and n-dodecyl group etc.) and salts thereof (sodium salt, lithium salt, potassium salt, magnesium salt, tetrabutyl ammonium salt, tetramethyl ammonium salt, tetraethyl ammonium salt, methyl pyridinium salt, ethyl pyridinium salt, butyl pyridinium salt, methyl quinolinium salt, ethyl quinolinium salt, butyl quinolinium salt and the like). Specific examples of the borate compound having three aryl groups in one molecule include monoalkyl triphenylboron, monoalkyl tri (p-chlorophenyl) boron, monoalkyl tri (p-fluorophenyl) boron, monoalkyl tri (3,5-bistrifluoro methyl) phenyl boron, monoalkyl tri [3,5-bis (1,1,1,3,3,3-hexafluoro-2-methoxy-2-propyl) phenyl] boron, monoalkyl tri (p-nitrophenyl) boron, monoalkyl tri (m-nitrophenyl) boron, monoalkyl tri (p-butylphenyl) boron, monoalkyl tri (m-butylphenyl) boron, monoalkyl tri (p-butyl oxyphenyl) boron, monoalkyl tri (m-butyl oxyphenyl) boron, monoalkyl tri (p-octyl oxyphenyl) boron and monoalkyl tri (m-octyl oxyphenyl) boron (the alkyl group is at least one selected from the group consisting of n-butyl group, n-octyl group and n-dodecyl group etc.) and salts thereof (sodium salt, lithium salt, potassium salt, magnesium salt, tetrabutyl ammonium salt, tetramethyl ammonium salt, tetraethyl ammonium salt, methyl pyridinium salt, ethyl pyridinium salt, butyl pyridinium salt, methyl quinolinium salt, ethyl quinolinium salt, butyl quinolinium salt and the like). Specific examples of the borate compound having four aryl groups in one molecule include tetraphenylboron, tetra kis (p-chlorophenyl) boron, tetra kis (p-fluorophenyl) boron, tetra kis (3,5-bistrifluoro methyl) phenyl boron, tetra kis [3,5-bis (1,1,1,3,3,3-hexafluoro-2-methoxy-2-propyl) phenyl] boron, tetra kis (p-nitrophenyl) boron, tetra kis (m-nitrophenyl) boron, tetra kis (p-butylphenyl) boron, tetra kis (m-butylphenyl) boron, tetra kis (p-butyl oxyphenyl) boron, tetra kis (m-butyl oxyphenyl) boron, tetra kis (p-octyl oxyphenyl) boron, tetra kis (m-octyl oxyphenyl) boron, (p-fluorophenyl) triphenylboron, (3,5-bis trifluoromethyl) phenyl triphenylboron, (p-nitrophenyl) triphenylboron, (m-butyl oxyphenyl) triphenylboron, (p-butyl oxyphenyl) triphenylboron, (m-octyl oxyphenyl) triphenylboron and (p-octyl oxyphenyl) triphenylboron, and salts thereof (sodium salt, lithium salt, potassium salt, magnesium salt, tetrabutyl ammonium salt, tetramethyl ammonium salt, tetraethyl ammonium salt, methyl pyridinium salt, ethyl pyridinium salt, butyl pyridinium salt, methyl quinolinium salt, ethyl quinolinium salt, butyl quinolinium salt and the like).

Among these aryl borate compounds, it is more preferable to use a borate compound having 3 or 4 aryl groups in one molecule from the viewpoint of storage stability. Further, these aryl borate compounds can be used alone or as a mixture of two or more.

Examples of sulfur-containing reductive inorganic compound include sulfites, bisulfites, pyrosulfites, thiosulfates, thionates and dithionite. Specific examples include sodium sulfite, potassium sulfite, calcium sulfite, ammonium sulfite, sodium bisulfite, potassium bisulfite, 3-mercaptopropyl trimethoxysilane, 2-mercaptobenzoxazole, decanethiol, thiobenzoic acid and the like.

Examples of nitrogen-containing reductive inorganic compound include nitrites, and specific examples include sodium nitrite, potassium nitrite, calcium nitrite, ammonium nitrite and the like.

Specific examples of barbituric acid derivative include salts (alkali metals or alkaline earth metals are preferred) of barbituric acid, 1,3-dimethyl barbituric acid, 1,3-diphenyl barbituric acid, 1,5-dimethyl barbituric acid, 5-butyl barbituric acid, 5-ethyl barbituric acid, 5-isopropyl barbituric acid, 5-cyclohexyl barbituric acid, 1,3,5-trimethyl barbituric acid, 1,3-dimethyl-5-ethyl barbituric acid, 1,3-dimethyl-n-butyl barbituric acid, 1,3-dimethyl-5-isobutyl barbituric acid, 1,3-dimethyl barbituric acid, 1,3-dimethyl-5-cyclopentyl barbituric acid, 1,3-dimethyl-5-cyclohexyl barbituric acid 1,3-dimethyl-5-phenyl barbituric acid, 1-cyclohexyl-1-ethyl barbituric acid, 1-benzyl-5-phenyl barbituric acid, 5-methyl barbituric acid, 5-propyl barbituric acid, 1,5-diethyl barbituric acid, 1-ethyl-5-methyl barbituric acid, 1-ethyl-5-isobutyl barbituric acid, 1,3-diethyl-5-butyl barbituric acid, 1-cyclohexyl-5-methyl barbituric acid, 1-cyclohexyl-5-ethyl barbituric acid, 1-cyclohexyl-5-octyl barbituric acid, 1-cyclohexyl-5-hexyl barbituric acid, 5-butyl-1-cyclohexyl barbituric acid, 1-benzyl-5-phenyl barbituric acid and thiobarbituric acids. Specifically, the salts of these barbituric acids include sodium 5-butyl barbiturate, sodium 1,3,5-trimethyl barbiturate, sodium 1-cyclohexyl-5-ethyl barbiturate and the like.

Specific examples of the halogen compound include dilauryl dimethyl ammonium chloride, lauryl dimethyl benzyl ammonium chloride, benzyl trimethyl ammonium chloride, tetramethyl ammonium chloride, benzyl dimethyl acetyl ammonium chloride, dilauryl dimethyl ammonium bromide and the like.

The photocurable composition of the present disclosure may not contain a chemical polymerization initiator and a chemical polymerization accelerator. The photocurable composition of the present disclosure may not contain a polymerization initiator system other than the photopolymerization system.

<Other Component>

Further, the dental photocurable composition of the present disclosure may contain a component other than above described (A) to (E) components within a range not to impair the effect of the present disclosure. For example, an excipient typified by fumed silica, benzophenone-based and benzotriazole-based ultraviolet absorbers, polymerization inhibitors such as hydroquinone, hydroquinone monomethyl ether and 2,5-ditershally butyl-4-methylphenol, chain transfer materials such as a-alkylstyrene compound, mercaptan compound such as n-butyl mercaptan and n-octyl mercaptan, and terpenoid compound such as limonene, myrsen, a-terpinene, 8-terpinene, y-terpinene, terpinoren, β-pinene and a-pinene, metal supplementary material such as aminocarboxylic acid chelating agent and phosphonic acid chelating agent, discoloration inhibitors, antibacterial materials, coloring pigments, water and solvent that can be mixed with water in any ratio, and other additives conventionally known in the art may be added as necessary and as desired.

A preparing method of the dental photocurable composition of the present disclosure is not particularly limited. Examples of a general preparing method of a dental photocurable composition include a method which comprises preparing a matrix by mixing (A) polymerizable monomer, (B) photosensitizer, (C) photoacid generator in the case of be contained and (D) photopolymerization accelerator in advance, kneading the matrix and (E) filler, and removing air bubbles under vacuum to prepare a uniform paste. In the present disclosure, it can be prepare by the above-described method without any problem.

The dental photocurable composition of the present disclosure is applied to a dental adhesive material, a dental composite resin, a dental core build-up material, a dental resin cement, a dental coating material, a dental sealant material, a dental manicure material, a dental splinting material, a dental hard resin, a dental CAD-CAM restoration material, a dental 3D printer material and the like.

<One Pack Type Dental Photocurable Composition>

When the dental photocurable composition of the present disclosure is used for one pack type dental photocurable composition, particularly as dental materials, it is preferable to use for a dental adhesive material, a dental composite resin, a dental core build-up material, a dental resin cement, a dental coating material, a dental sealant material, a dental manicure material, a dental splinting material, a dental CAD-CAM restoration material and a dental 3D printer material, it is particularly preferable to use for a dental adhesive material, a dental composite resin, a dental core build-up material, a dental resin cement, a dental coating material, a dental sealant material, a dental manicure material and a dental splinting material. In the case of a one pack type dental photocurable composition, it can be expected that there are few technical errors and the risk of contamination with air bubbles is reduced.

<Two Packs Type Dental Photocurable Composition>

When the dental photocurable composition of the present disclosure is used for two packs type dental photocurable composition, particularly as dental materials, it is preferable to use for a dental adhesive material, a dental composite resin, a dental core build-up material, a dental resin cement, a dental coating material, a dental sealant material, a dental manicure material, a dental splinting material, a dental CAD-CAM restoration material and a dental 3D printer material, it is particularly preferable to use for a dental composite resin, a dental core build-up material and a dental resin cement. The two packs type dental material is used by kneading the two packs including a first paste and a second paste immediately before use. The kneading is performed by mixing the first paste and the second paste in a volume ratio of 0.9 to 1.1:1.0 or a mass ratio of 0.8 to 1.2:1.0, preferably an equal volume ratio. The kneading method may be a known method such as manual kneading using a spatula and the like, or automatic kneading via a dedicated shaking device or a static mixer. Since the components can be separated into two packs, compounds that cannot be compounded in the same paste can be compounded separately, therefore the storage stability is excellent.

The dental photocurable composition of the present disclosure may comprise only (A) polymerizable monomer, (B) photosensitizer, (C) photoacid generator, (D) photopolymerization accelerator and (E) filler. Further, as the components other than (A) to (E), only one or more of the above-mentioned components may be contained.

Examples

Hereinafter, examples of the present disclosure are specifically described. However, the present disclosure is not intended to be limited to these Examples.

The materials used in Examples and Comparative examples and their abbreviations are listed below. [(A) Polymerizable Monomer]

Bis-GMA: 2,2-bis [4-(3-methacryloyloxy-2-hydroxypropoxy) phenyl] propane D2.6E: 2,2-bis (4-(meth) acryloyloxy polyethoxyphenyl) propane in which the average addition mole number of ethoxy groups is 2.6

UDMA: N,N-(2,2,4-trimethyl hexamethylene) bis [2-(aminocarboxy) ethanol]methacrylate NPG: neopentyl glycol dimethacrylate TEGDMA: triethyleneglycol dimethacrylate GDMA: glycerin dimethacrylate MDP: 10-methacryloyloxydecyl dihydrogen phosphate

[(B) Photosensitizer

CQ: camphorquinone

[(C) Photoacid Generator]

<Salt of an Anion Having an Organic Group in which at Least One H is Substituted with F and One or More Atoms of P, B, Al, S, and Ga, and an Aryl Iodonium Cation>

C1: bis (4-tert-butylphenyl) iodonium nonafluorobutane sulfonate

[Chemical formula 4]

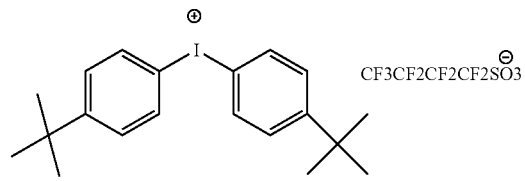

C2: bis (4-tert-butylphenyl) iodonium tris (pentafluoropropyl) trifluorophosphate

[Chemical formula 5]

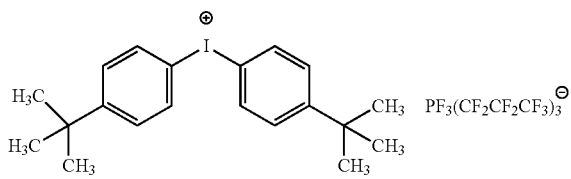

C3: p-cumenyl (p-tolyl) iodonium tris (pentafluoroethyl) trifluorophosphate

[Chemical formula 6]

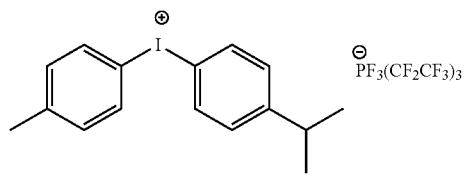

C4: bis (4-n-dodecylphenyl) iodonium tetrakis (pentafluorophenyl) borate

[Chemical formula 7]

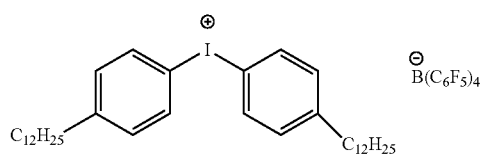

C5: bis [4-(tert-butyl) phenyl] iodonium tetra (nonafluoro-tert-butoxy) aluminate

[Chemical formula 8]

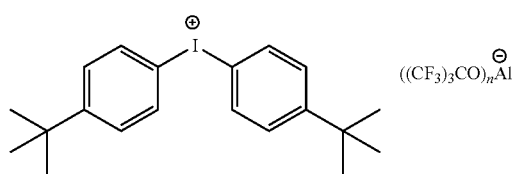

C6: bis (4-isopropylphenyl) iodonium tetra (pentafluorophenyl) gallate

[Chemical formula 9]

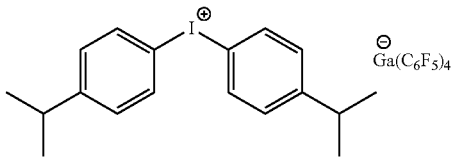

<Salt of an Anion Having an Organic Group and One or More Atoms of P, B, Al, S, and Ga, and an Aryl Iodonium Cation>

C11: bis (4-tert-butylphenyl) iodonium-p-toluenesulfonate

[Chemical fomula 10]

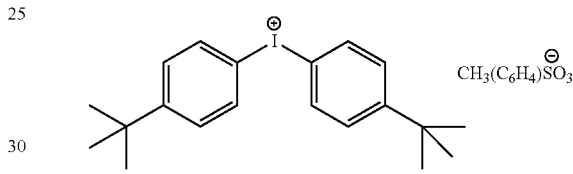

<Photoacid Generator Other than a Salt of an Anion Having an Organic Group and One or More Atoms of P, B, Al, S, and Ga, and an Aryl Iodonium Cation>

C21: bis (4-tert-butylphenyl) iodonium hexafluorophosphate

[Chemical formula 11]

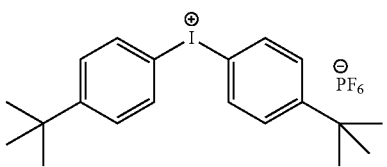

C22: 2,4,6-tris-(trichloromethyl)-1,3,5-triazine

[Chemical formula 12]

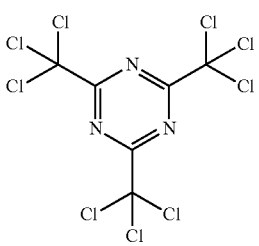

C23: diphenyliodonium-2-carboxylate monohydrate

[Chemical formula 13]

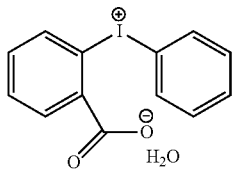

[(D) Photopolymerization Accelerator]
[(D1) Aliphatic Tertiary Amine Compound Represented by Formula (1)]
<Aliphatic Tertiary Amine Having One Substituent Consisting of Three or More Carbons Having an Electron-Withdrawing Group at α-Carbon and/or β-Carbon of an Amine Starting from N>

D1-1: N,N-diisopropylaminoethyl methacrylate

[Chemical formula 14]

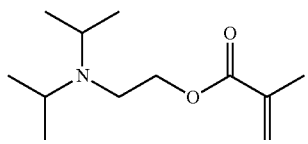

D1-2: 3-isopropyl-2-methyl-7-oxo-6,11-dioxo-3,8-diazatridecane-13-yl methacrylate

[Chemical formula 15]

D1-3: 2-(((2-(dibutylamino) ethoxy) carbonyl) amino) ethyl methacrylate

[Chemical formula 16]

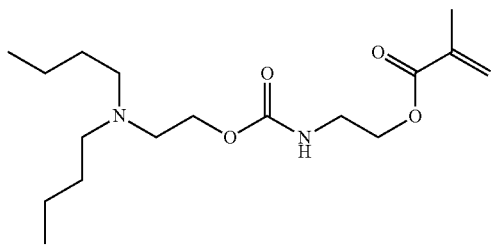

D1-4: 1-[(3,3)-diphenylpropyl) (niethyl) aminol-2-methyl]-2-propanol

[Chemical formula 17]

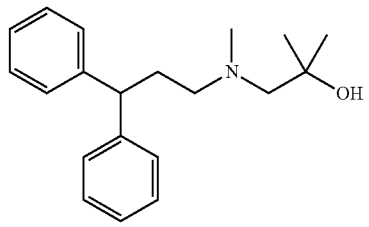

<Aliphatic Tertiary Amine Having Two or More Substituents Consisting of Three or More Carbons Having an Electron-Withdrawing Group at α-Carbon and/or β-Carbon of an Amine Starting from N>

D2-1: Triisopanol Amine

[Chemical formula 18]

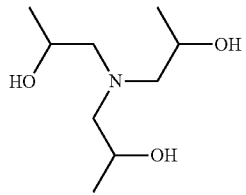

D2-2: Diethylbenzylimino Diacetate

[Chemical formula 19]

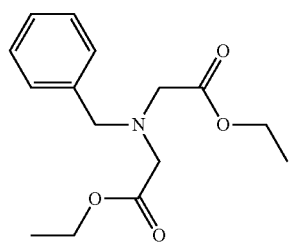

D2-3: 11-benzyl-7,15-dioxo-3,8,14,19-tetraoxo-6,11,16-triazahenicosan-1,21-diylbis (2-methacrylate)

[Chemical formula 20]

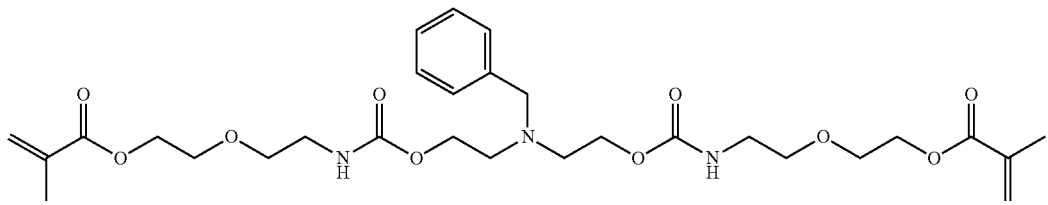

<Aliphatic Tertiary Amine Having Two or More Aryls which May have a Substituent as a Substituent of N>

D3-1: 2-benzyl-6-oxo-1-phenyl-5,10-dioxo-2,7-diazadodecane-1²-yl methacrylate

[Chemical formula 21]

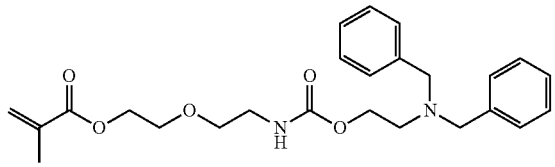

D3-2: N,N-dibenzylglycine ethyl ester

[Chemical formula 22]

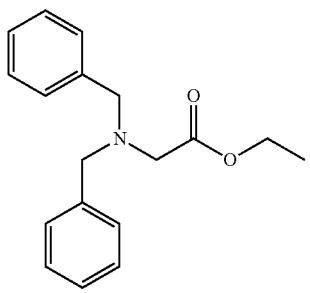

D3-3: dibenzylaminopropyl methacrylate

[Chemical formula 23]

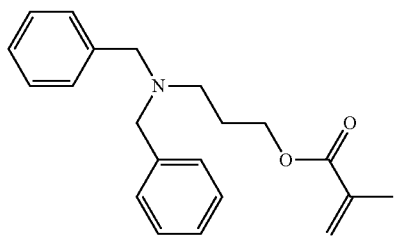

D3-4: (S)-(+)-2-(dibenzylamino)-3-phenyl-1-propanol

[Chemical formula 24]

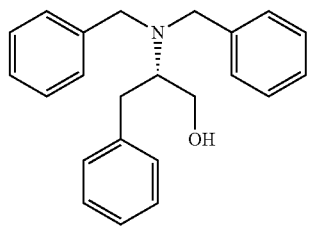

D3-5: dibenzylaminopropanol

[Chemical formula 25]

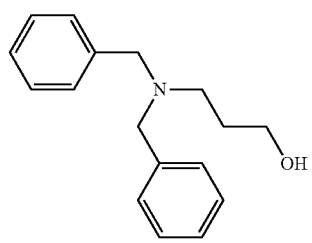

D3-6: tribenzylamine

[Chemical formula 26]

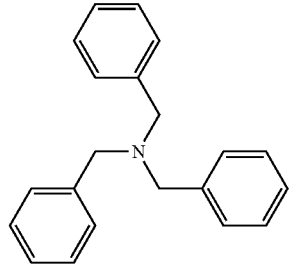

D3-7: 2-(((2-(dibenzylamino) ethoxy) carbonyl) amino)-2-methylpropane-1,3-diyl dimethacrylate

[Chemical formula 27]

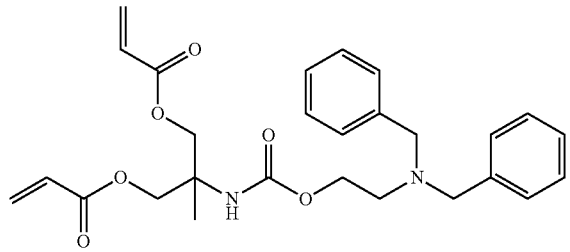

D3-8: 3-(N,N-dibenzylamino) propyltriethoxysilane

[Chemical formula 28]

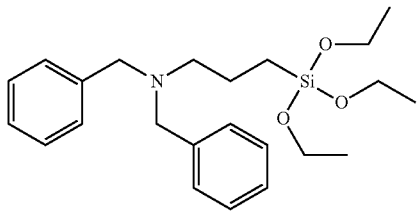

<Other Aliphatic Tertiary Amine>
<<Aliphatic Tertiary Amine Compound Having No Primary Hydroxyl Group>>
DMAEMA: N,N-Dimethylamino Ethylmethacrylate
<<Aliphatic Tertiary Amine Compound Having Two Primary Hydroxyl Groups>>
MDEOA: Methyl Diethanolamine
<<Aliphatic Tertiary Amine Compound Having Three Primary Hydroxyl Groups>>
TEA: Triethanolamine
<Aromatic Tertiary Amine Compound>
DMBE: N,N-dimethylaminobenzoate ethyl
DEPT: N,N-di(2-hydroxyethyl)-p-toluidine
[(E) Filler]
The preparing method of each filler used for preparing the dental photocurable composition is shown below.
<(E1) Hydrophobized Silica Fine Particle Having an Average Diameter of Primary Particle of 1 to 40 nm>
<<Hydrophobized Fine Particle Surface-Treated with Dimethylsilicone Oil or Surface-Treated by Covalent Bonding with a Functional Group Selected from Trimethylsilyl Group, Dimethylsilyl Group, Methylsilyl Group, and Linear Alkylsilyl Group Having 3 to 18 Carbon Atoms>>
Filler E11: Aerosil R972 (manufactured by Evonik, average primary particle diameter: 16 nm, hydrophobization method: dimethylsilyl group)
Filler E12: Aerosil R8200 (manufactured by Evonik, average primary particle diameter: 12 nm, hydrophobization method: trimethylsilyl group)
Filler E13: Aerosil R805 (manufactured by Evonik, average primary particle diameter: 12 nm, hydrophobization method: octylsilyl group)
Filler E14: Aerosil R202 (manufactured by Evonik, average primary particle diameter: 14 nm, hydrophobization method: dimethylsilicone)

Filler E15
A silane coupling treatment solution prepared by stirring 50.0 g of water, 35.0 g of ethanol, and 10.0 g of trimethoxyoctadecylsilane as a silane coupling material at room temperature for 2 hours was added to 100.0 g of Aerosil 200 (manufactured by Evonik, average primary particle diameter: 12 nm) and stirred for 30 minutes. Thereafter, a heat treatment was performed at 100° C. for 15 hours to obtain filler E15.
<<Hydrophobized Fine Particle Surface-Treated with Method Other than Dimethylsilicone Oil, Trimethylsilyl Group, Dimethylsilyl Group, Methylsilyl Group, and Linear Alkylsilyl Group Having 3 to 18 Carbon Atoms>>
Filler E21: Aerosil R7200 (manufactured by Evonik, average primary particle diameter: 12 nm, hydrophobization method: methacryloxysilyl group)
Filler E22
A silane coupling treatment solution prepared by stirring 50.0 g of water, 35.0 g of ethanol, and 10.0 g of 8-methacryloyloxyoctyl trimethoxysilane as a silane coupling material at room temperature for 2 hours was added to 100.0 g of Aerosil OX50 (manufactured by Evonik, average particle diameter: 40 nm) and stirred for 30 minutes. Thereafter, a heat treatment was performed at 100° C. for 15 hours to obtain filler E22.
<(E2) Inorganic Filler Having an Average Diameter of Primary Particle of 0.1 to 10 μm> Filler E31
A silane coupling treatment solution prepared by stirring 50.0 g of water, 35.0 g of ethanol, and 3.0 g of 3-methacryloyloxypropyl trimethoxysilane as a silane coupling material at room temperature for 2 hours was added to 100.0 g of fluoroaluminosilicate glass (average particle diameter: 1.1 μm) and stirred for 30 minutes. Thereafter, a heat treatment was performed at 100° C. for 15 hours to obtain filler E31.
Filler E32
A silane coupling treatment solution prepared by stirring 50.0 g of water, 35.0 g of ethanol, and 5.0 g of 3-methacryloyloxypropyl trimethoxysilane as a silane coupling material at room temperature for 2 hours was added to 100.0 g of zirconium silicate filler (average particle diameter: 0.6 μm, zirconia: 85% by mass, silica: 15% by mass) and stirred for 30 minutes. Thereafter, a heat treatment was performed at 100° C. for 15 hours to obtain filler E32.
Filler E33
After various raw materials of silica dioxide, aluminum oxide, boron oxide, sodium fluoride, and strontium carbonate were mixed, the mixture was melted to obtain glass A (glass composition: 22.5% by mass of $SiO_2$, 20.0% by mass of $Al_2O_3$, 12.3% by mass of $B_2O_3$, 35.7% by mass of SrO, 2.5% by mass of $Na_2O$, and 7.0% by mass of F). The obtained glass A was pulverized using a vibration mill for 100 hours, and then pulverized using a wet bead mill for 3 hours.
(Polysiloxane Treatment)
Then, 4.5 g of a low condensate of silane compound "MKC SILICATE MS56S" ($SiO_2$ content: 56.0% by mass, degree of polymerization: 2 to 100, manufactured by Mitsubishi Chemical Corporation) was added to 100 g of the obtained pulverized product, and stirred-mixed for 90 minutes. After mixing for a predetermined time, the prepared treated slurry was aged in a hot air dryer at 50° C. for 40 hours, then heated to 150° C. and held for 6 hours, then cooled to obtain a heat treated product. The obtained heat-treated product was placed in a Henschel mixer and crushed at 1800 rpm for 5 minutes. After pulverization, a polysiloxane-treated product having a surface coated with polysiloxane and having good fluidity was obtained.

(Acidic Polymer Treatment)

Then, 100 g of the polysiloxane-treated product was put into a Henschel mixer, and 16.0 g of a polyacrylic acid aqueous solution (polymer concentration: 13% by mass, weight average molecular weight: 20,000, manufactured by Nacalai Co., Ltd.) was sprayed from above while stirring. After spraying, the powder taken out from the mixer was heated in a hot air dryer at 100° C. for 3 hours to obtain a polysiloxane-polyacrylic acid-treated product.

(Silane Treatment)

A silane coupling treatment solution prepared by stirring 100.0 g of water, 80.0 g of ethanol, 0.003 g of phosphoric acid, and 12.0 g of 3-methacryloyloxypropyl trimethoxysilane as a silane coupling agent at room temperature for 2 hours was added to 100.0 g of the polysiloxane-polyacrylic acid-treated product and stirred for 30 minutes. Thereafter, a heat treatment was performed at 100° C. for 15 hours to obtain filler E33.

<Filler other than (E1) and (E2)>

Filler E34

A silane coupling treatment solution prepared by stirring 100.0 g of water, 80.0 g of ethanol, 0.003 g of phosphoric acid, and 12.0 g of 3-methacryloyloxypropyl trimethoxysilane as a silane coupling agent at room temperature for 2 hours was added to 100.0 g of Aerosil AluC (manufactured by Evonik), which is fine particle alumina, and stirred for 30 minutes. Thereafter, a heat treatment was performed at 100° C. for 15 hours to obtain filler E34.

[Chemical Polymerization Initiator]

CHP: cumene hydroperoxide

TMBH: 1,1,3,3-tetramethylbutyl hydroperoxide

TPE: 1,1,3,3-tetramethylbutyl peroxy-2-ethylhexanoate

BPO: benzoyl peroxide

[Chemical Polymerization Accelerator]

PTU: (2-pyridyl) thiourea

BTU: N-benzoylthiourea

DEPT: N,N-di (2-hydroxyethyl)-p-toluidine

COA: acetylacetone copper

VOAA: vanadyl acetylacetonate

[UV Absorber]

BT: 2-(2-hydroxy-5-methylphenyl) benzotriazole

[Polymerization Inhibitor]

BHT: 2,6-di-t-butyl-4-methylphenol

MeHQ: p-methoxyphenol

[Fluorescent Agent]

FA: 2,5-dihydroxyterephthalate diethyl

<Preparing Method of One Pack Type Dental Photocurable Composition>

All components shown in Tables 1 to 2 other than the filler (E) were put into a wide mouthed plastic container and mixed by using a mix rotor VMRC-5 under the condition of 100 rpm for 48 hours to prepare a matrix. Then, the matrix and the filler (E) were put into a kneader, stirred uniformly, and then defoamed under vacuum to prepare one pack type dental photocurable composition in paste form. Thereafter, the one pack type dental photocurable composition was filled in the syringe container of BEAUTIFIL Flow Plus manufactured by SHOFU INC. In the tables 1 to 2, the content (parts by mass) of each component is indicated by the numerical value in parentheses after the abbreviation of each component.

TABLE 1

| One pack type dental photocurable composition | (A) Polymerizable monomer | (B) Photo sensitizer | (C) Photo acid generator | (D) Photopolymerization accelerator | |
|---|---|---|---|---|---|
| | | | | (D1) Aliphatic tertiary amine compound represented by formula (1) | Photopolymerization accelerator other than (D1) |
| Example A1 | UDMA(70), TEGDMA(30) | CQ(0.2) | C2(3) | D3-1(1) | — |
| Example A2 | UDMA(70), TEGDMA(30) | CQ(0.2) | C2(2) | D3-2(0.8) | — |
| Example A3 | Bis-GMA(60), TEGDMA(40) | CQ(0.1) | C2(3) | D3-3(1) | — |
| Example A4 | Bis-GMA(60), TEGDMA(40) | CQ(0.3) | C2(0.3) | D3-4(1) | — |
| Example A5 | Bis-GMA(60), TEGDMA(30), MDP(10) | CQ(0.4) | C2(0.8) | D3-3(0.8) | — |
| Example A6 | UDMA(60), TEGDMA(40) | CQ(0.2) | C2(2) | D3-6(1) | — |
| Example A7 | UDMA(60), TEGDMA(40) | CQ(0.1) | C2(2) | D3-7(1) | — |
| Example A8 | Bis-GMA(60), TEGDMA(40) | CQ(0.01) | C1(12) | D3-8(8) | — |
| Example A9 | Bis-GMA(60), TEGDMA(40) | CQ(1) | C1(0.2) | D3-6(1) | — |
| Example A10 | Bis-GMA(60), TEGDMA(40) | CQ(3) | — | D3-6(5) | — |
| Example A11 | Bis-GMA(40), UDMA(20), TEGDMA(40) | CQ(0.3) | — | D3-1(3) | DMBE(0.3) |
| Example A12 | Bis-GMA(60), TEGDMA(40) | CQ(1) | C2(0.05) | D3-6(1) | — |
| Example A13 | Bis-GMA(40), UDMA(20), NPG(40) | CQ(0.2) | C2(12) | D3-6(1) | — |
| Example A14 | Bis-GMA(60), TEGDMA(40) | CQ(0.3) | C11(1.5) | D3-6(1.5) | — |
| Example A15 | Bis-GMA(60), TEGDMA(40) | CQ(0.3) | C21(1) | D3-6(1.5) | — |
| Example A16 | Bis-GMA(60), TEGDMA(40) | CQ(0.3) | C22(1) | D3-6(2) | — |
| Example A17 | Bis-GMA(60), TEGDMA(40) | CQ(0.3) | C23(1) | D3-6(2) | — |
| Example A18 | Bis-GMA(60), TEGDMA(40) | CQ(0.3) | C21(0.2) | D3-3(1.5) | — |
| Example A19 | Bis-GMA(60), TEGDMA(40) | CQ(0.3) | C22(0.2) | D3-3(1.5) | — |
| Example A20 | Bis-GMA(60), TEGDMA(40) | CQ(0.3) | C23(0.2) | D3-6(1.5) | — |
| Example A21 | D2.6E(80), TEGDMA(20) | CQ(0.2) | C2(1) | D3-6(0.05) | — |
| Example A22 | UDMA(60), TEGDMA(20), GDMA(20) | CQ(0.2) | C3(1) | D3-6(22) | — |
| Example A23 | Bis-GMA(60), TEGDMA(40) | CQ(0.3) | C4(1) | D3-6(0.9) | — |
| Example A24 | Bis-GMA(50), TEGDMA(20), GDMA(20), MDP(10) | CQ(0.1) | C6(2) | D3-6(3) | — |
| Example A25 | Bis-GMA(60), TEGDMA(40) | CQ(0.3) | C5(1) | D3-6(3) | — |
| Example A26 | Bis-GMA(60), TEGDMA(30), MDP(10) | CQ(0.3) | C6(1) | D3-6(3) | — |
| Example A27 | Bis-GMA(60), TEGDMA(40) | CQ(0.3) | C2(0.2) | D1-1(1) | — |
| Example A28 | UDMA(70), TEGDMA(30) | CQ(0.3) | C3(0.5) | D1-2(1) | — |
| Example A29 | UDMA(70), TEGDMA(30) | CQ(0.2) | C4(0.5) | D1-3(1) | — |
| Example A30 | Bis-GMA(60), TEGDMA(40) | CQ(0.3) | C5(2) | D1-4(1) | — |

TABLE 1-continued

| One pack type dental photocurable composition | (A) Polymerizable monomer | (B) Photo sensitizer | (C) Photo acid generator | (D) Photopolymerization accelerator (D1) Aliphatic tertiary amine compound represented by formula (1) | Photopolymerization accelerator other than (D1) |
|---|---|---|---|---|---|
| Example A31 | Bis-GMA(55), TEGDMA(25), MDP(20) | CQ(0.5) | C6(0.5) | D2-1(1) | — |
| Example A32 | Bis-GMA(60), TEGDMA(40) | CQ(0.3) | C1(3) | D2-2(1) | — |
| Example A33 | D2.6E(80), TEGDMA(20) | CQ(0.3) | C1(0.5) | D2-3(1) | — |
| Example A34 | UDMA(70), TEGDMA(30) | CQ(0.2) | C5(2) | D3-6(3) | — |
| Example A35 | Bis-GMA(60), TEGDMA(40) | CQ(0.3) | C6(2) | D3-6(3) | — |
| Example A36 | Bis-GMA(60), TEGDMA(40) | CQ(0.3) | C5(1) | D3-1(0.5) | DMBE(0.3) |
| Example A37 | Bis-GMA(60), TEGDMA(40) | CQ(0.3) | C5(0.4) | D3-1(0.5) | DMBE(0.3) |
| Example A38 | Bis-GMA(40), UDMA(20), NPG(40) | CQ(0.1) | C2(3) | D3-6(3) | — |
| Comparative Example CA1 | Bis-GMA(60), TEGDMA(40) | — | C2(2) | D3-4(1) | — |
| Comparative Example CA2 | Bis-GMA(60), TEGDMA(40) | CQ(0.5) | C3(5) | — | — |
| Comparative Example CA3 | Bis-GMA(60), TEGDMA(40) | CQ(0.2) | C5(2) | D3-1(1) | — |
| Comparative Example CA4 | Bis-GMA(60), TEGDMA(40) | CQ(0.2) | C5(2) | — | MDEOA(1) |
| Comparative Example CA5 | Bis-GMA(60), TEGDMA(40) | CQ(0.3) | C5(2) | — | TEA(1) |
| Comparative Example CA6 | Bis-GMA(60), TEGDMA(40) | CQ(0.3) | C5(2) | — | DMAEMA(1) |

TABLE 2

| One pack type dental photocurable composition | (E) Filler (E1) Hydrophobized silica fine particle having an average diameter of primary particle of 1 to 40 nm | (E2) Inorganic filler having an average diameter of primary particle of 0.1 to 10 μm | Filler other than (E1) and (E2) | Polymerization inhibitor | Others |
|---|---|---|---|---|---|
| Example A1 | E11(0.2) | E31(200) | — | MeHQ(0.005) | FA(0.01) |
| Example A2 | E11(0.8) | E31(300) | — | MeHQ(0.005) | FA(0.01) |
| Example A3 | E11(1) | E32(300) | — | MeHQ(0.005) | FA(0.01) |
| Example A4 | E11(15) | E31(300) | — | MeHQ(0.005) | FA(0.01) |
| Example A5 | E11(30) | E32(200) | — | MeHQ(0.005) | — |
| Example A6 | E11(42) | E32(20) | — | MeHQ(0.005) | FA(0.01) |
| Example A7 | E12(10) | E32(450) | E34(10) | MeHQ(0.005) | — |
| Example A8 | E12(15) | E33(300) | — | MeHQ(0.005) | FA(0.01) |
| Example A9 | E13(15) | E32(200), E33(20) | E34(5) | MeHQ(0.005) | FA(0.01) |
| Example A10 | E15(15) | E31(250) | E34(15) | MeHQ(0.005) | FA(0.01) |
| Example A11 | E14(15) | E32(280) | — | MeHQ(0.005) | FA(0.01) |
| Example A12 | E12(15) | E31(280) | — | MeHQ(0.005) | FA(0.01) |
| Example A13 | E15(15) | E32(280) | — | MeHQ(0.005) | FA(0.01) |
| Example A14 | E12(15) | E33(280) | — | MeHQ(0.005) | FA(0.01) |
| Example A15 | E15(15) | E31(280) | — | MeHQ(0.005) | FA(0.01) |
| Example A16 | E14(15) | E32(280) | — | MeHQ(0.005) | FA(0.01) |
| Example A17 | E11(15) | E31(280) | — | MeHQ(0.005) | FA(0.01) |
| Example A18 | E15(15) | E31(280) | — | MeHQ(0.005) | FA(0.01) |
| Example A19 | E14(15) | E32(280) | — | MeHQ(0.005) | FA(0.01) |
| Example A20 | E11(15) | E31(280) | — | MeHQ(0.005) | FA(0.01) |
| Example A21 | E14(15) | E32(280) | — | MeHQ(0.005) | FA(0.01) |
| Example A22 | E11(15) | E33(280) | — | MeHQ(0.005) | FA(0.01) |
| Example A23 | E11(20) | — | — | MeHQ(0.005) | FA(0.01) |
| Example A24 | E11(20) | E32(15) | — | MeHQ(0.005) | — |
| Example A25 | E11(20) | E31(20) | E34(10) | MeHQ(0.005) | FA(0.01) |
| Example A26 | E11(20) | E31(70) | — | MeHQ(0.005) | — |
| Example A27 | E15(15) | E32(280) | E34(10) | MeHQ(0.005) | FA(0.01) |
| Example A28 | E15(15) | E31(280) | — | MeHQ(0.005) | — |
| Example A29 | E14(15) | E32(280) | — | MeHQ(0.005) | — |
| Example A30 | E12(15) | E33(280) | — | MeHQ(0.005) | FA(0.01) |
| Example A31 | E15(15) | E32(280) | — | MeHQ(0.005) | — |
| Example A32 | E14(12) | E31(280) | — | MeHQ(0.005) | FA(0.01) |
| Example A33 | E11(12) | E32(280) | — | MeHQ(0.005) | — |
| Example A34 | E21(15) | E31(250) | — | MeHQ(0.005) | FA(0.01) |
| Example A35 | E22(20) | E33(250) | — | MeHQ(0.005) | FA(0.01) |
| Example A36 | E12(15) | E32(280) | — | MeHQ(0.005) | FA(0.01) |
| Example A37 | E12(15) | E32(280) | — | MeHQ(0.005) | FA(0.01), BT(0.5) |
| Example A38 | E15(15) | E32(280) | — | — | FA(0.01), BT(0.5) |
| Comparative Example CA1 | E12(15) | E32(280) | — | MeHQ(0.005) | — |
| Comparative Example CA2 | E12(15) | E32(280) | — | MeHQ(0.005) | — |
| Comparative Example CA3 | — | E32(280) | — | MeHQ(0.005) | — |
| Comparative Example CA4 | E12(15) | E33(280) | — | MeHQ(0.005) | — |
| Comparative Example CA5 | E12(15) | E33(280) | — | MeHQ(0.005) | — |
| Comparative Example CA6 | E12(15) | E33(280) | — | MeHQ(0.005) | — |

<Preparing Method of Two Packs Type Dental Photocurable Composition>

All components shown in Tables 3 to 4 other than the filler (E) were put into a wide mouthed plastic container and mixed by using a mix rotor VMRC-5 under the condition of 100 rpm for 48 hours to prepare a matrix. Then, the matrix and the filler (F) were put into a kneader, stirred uniformly, and then defoamed under vacuum to prepare a first paste and a second paste, and then the first paste and the second paste were filled into a double syringe (5 mL) manufactured by Mixpack Co., Ltd. to prepare a dental photocurable composition. In the Tables 3 to 4, the content (parts by mass) of each component is indicated by the numerical value in parentheses after the abbreviation of each component.

TABLE 3

| Two packs type dental photocurable composition | | (A) Polymerizable monomer | (B) Photo sensitizer | (C) Photo acid generator | (D) Photopolymerization accelerator | |
|---|---|---|---|---|---|---|
| | | | | | (D1) Aliphatic tertiary amine compound represented by formula (1) | Photopolymerization accelerator other than (D1) |
| Example B1 | First paste | UDMA(70), TEGDMA(30) | CQ (0.6) | C2(3) | D3-1(1) | — |
| | Second paste | UDMA(70), TEGDMA(30) | — | — | — | — |
| Example B2 | First paste | UDMA(70), TEGDMA(30) | CQ (0.6) | — | D3-2(1) | — |
| | Second paste | UDMA(70), TEGDMA(30) | — | C2(2) | — | — |
| Example B3 | First paste | Bis-GMA(60), TEGDMA(40) | CQ (0.6) | — | D3-3(1) | — |
| | Second paste | Bis-GMA(60), TEGDMA(40) | — | C2(3) | — | — |
| Example B4 | First paste | Bis-GMA(60), TEGDMA(40) | CQ (0.6) | — | D3-4(1) | — |
| | Second paste | Bis-GMA(60), TEGDMA(40) | — | C2 (0.4) | — | — |
| Example B5 | First paste | Bis-GMA(60), TEGDMA(30), MDP(10) | CQ (0.6) | C2 (0.8) | D3-5(1) | — |
| | Second paste | Bis-GMA(60), TEGDMA(40) | — | — | — | — |
| Example B6 | First paste | UDMA(60), TEGDMA(40) | CQ (0.6) | C2(2) | D3-6(1) | — |
| | Second paste | UDMA(60), TEGDMA(40) | — | — | — | — |
| Example B7 | First paste | UDMA(60), TEGDMA(40) | — | C2(2) | D3-7(1) | — |
| | Second paste | UDMA(60), TEGDMA(40) | CQ (0.6) | — | — | — |
| Example B8 | First paste | Bis-GMA(60), TEGDMA(40) | CQ (0.01) | C1 (21) | D3-8(1) | — |
| | Second paste | Bis-GMA(60), TEGDMA(40) | — | — | — | — |
| Example B9 | First paste | Bis-GMA(60), TEGDMA(40) | CQ(3) | — | — | — |
| | Second paste | Bis-GMA(60), TEGDMA(40) | — | — | D3-6(5) | — |
| Example B10 | First paste | Bis-GMA(60), TEGDMA(40) | CQ(1) | C2 (0.08) | D3-6(1) | — |
| | Second paste | Bis-GMA(60), TEGDMA(40) | — | — | — | — |
| Example B11 | First paste | Bis-GMA(60), TEGDMA(40) | CQ (0.6) | C11 (1.5) | D3-6 (1.5) | — |
| | Second paste | Bis-GMA(60), TEGDMA(40) | — | — | — | — |
| Example B12 | First paste | Bis-GMA(60), TEGDMA(40) | CQ (0.6) | C21 (2) | D3-6 (1.5) | — |
| | Second paste | Bis-GMA(60), TEGDMA(40) | — | — | — | — |
| Example B13 | First paste | D2.6E(80), TEGDMA(20) | — | C2(1) | D3-6 (0.1) | — |
| | Second paste | D2.6E(80), TEGDMA(20) | CQ (0.6) | — | — | — |
| Example B14 | First paste | UDMA(70), TEGDMA(30) | — | C3(1) | D3-6 (22) | — |
| | Second paste | UDMA(70), TEGDMA(30) | CQ (0.6) | — | — | — |
| Example B15 | First paste | Bis-GMA(60), TEGDMA(40) | CQ (0.6) | C2 (0.2) | D1-1(1) | — |
| | Second paste | Bis-GMA(60), TEGDMA(40) | — | — | — | — |
| Example B16 | First paste | UDMA(70), TEGDMA(30) | CQ (0.6) | C3 (0.5) | D1-2(1) | — |
| | Second paste | UDMA(70), TEGDMA(30) | — | — | — | — |
| Example B17 | First paste | UDMA(70), TEGDMA(30) | CQ (0.6) | C4 (0.5) | D1-3(1) | — |
| | Second paste | UDMA(70), TEGDMA(30) | — | — | — | — |
| Example B18 | First paste | Bis-GMA(60), TEGDMA(20), MDP(20) | CQ (0.6) | C6 (0.5) | D2-1(1) | — |
| | Second paste | Bis-GMA(60), TEGDMA(40) | — | — | — | — |
| Example B19 | First paste | D2.6E(80), TEGDMA(20) | CQ (0.6) | C1 (0.5) | D2-3(1) | — |
| | Second paste | D2.6E(80), TEGDMA(20) | — | — | — | — |
| Example B20 | First paste | UDMA(70), TEGDMA(30) | CQ (0.6) | C5(2) | D3-6(3) | — |
| | Second paste | UDMA(70), TEGDMA(30) | — | — | — | — |
| Example B21 | First paste | Bis-GMA(60), TEGDMA(40) | CQ (0.6) | C6(2) | D3-6(3) | — |
| | Second paste | Bis-GMA(60), TEGDMA(40) | — | — | — | — |
| Example B22 | First paste | Bis-GMA(60), TEGDMA(40) | CQ (0.6) | C5(2) | — | DMBE (0.3) |
| | Second paste | Bis-GMA(60), TEGDMA(40) | — | — | D3-1(1) | — |
| Example B23 | First paste | Bis-GMA(60), TEGDMA(40) | CQ (0.6) | — | D3-1(1) | DMBE (0.3) |
| | Second paste | Bis-GMA(60), TEGDMA(40) | — | C5(2) | — | — |
| Comparative Example CB1 | First paste | Bis-GMA(60), TEGDMA(40) | CQ (0.6) | C5(2) | D3-1(1) | — |
| | Second paste | Bis-GMA(60), TEGDMA(40) | — | — | — | — |
| Comparative Example CB2 | First paste | Bis-GMA(60), TEGDMA(40) | CQ (0.6) | C5(2) | — | MDEOA (2) |
| | Second paste | Bis-GMA(60), TEGDMA(40) | — | — | — | — |
| Comparative Example CB3 | First paste | Bis-GMA(60), TEGDMA(40) | CQ (0.6) | C5(2) | — | TEA(2) |
| | Second paste | Bis-GMA(60), TEGDMA(40) | — | — | — | — |
| Comparative Example CB4 | First paste | Bis-GMA(60), TEGDMA(40) | CQ (0.6) | C5(2) | — | DMAEMA (2) |
| | Second paste | Bis-GMA(60), TEGDMA(40) | — | — | — | — |

TABLE 4

| Two packs type dental photocurable composition | | Chemical initiator or Chemical polymerization accelerator | (E) Filler | | | Polymerization inhibitor | Others |
|---|---|---|---|---|---|---|---|
| | | | (E1) Hydrophobized silica fine particle having an average diameter of primary particle of 1 to 40 nm | (E2) Inorganic filler having an average diameter of primary particle of 0.1 to 10 μm | Filler other than (E1) and (E2) | | |
| Example B1 | First paste | PTU(1.0) | E11(0.1) | E31(250) | — | BHT(0.1) | FA(0.01) |
| | Second paste | CHP(1.5) | E11(0.1) | E31(250) | — | BHT(0.1) | — |
| Example B2 | First paste | PTU(1.0) | E11(0.4) | E31(200) | — | BHT(0.1) | FA(0.05) |
| | Second paste | TMBH(2) | E11(0.4) | E31(200) | — | BHT(0.1) | — |
| Example B3 | First paste | BTU(1.0), VOA(0.01) | E11(1) | E32(200) | — | BHT(0.1) | FA(0.05) |
| | Second paste | CHP(1.5) | E11(1) | E32(200) | — | BHT(0.1) | — |
| Example B4 | First paste | PTU(1.0), COA(0.1) | E11(15) | E31(200) | — | BHT(0.1) | FA(0.01) |
| | Second paste | TMBH(2) | E11(15) | E31(200) | — | BHT(0.1) | — |
| Example B5 | First paste | PTU(1.0), COA(0.1) | E11(30) | E32(200) | — | BHT(0.1) | — |
| | Second paste | CHP(1.5) | E11(30) | E32(200) | — | BHT(0.1) | — |
| Example B6 | First paste | BTU(1), VOA(0.01) | E11(42) | E32(20) | — | BHT(0.1) | FA(0.05) |
| | Second paste | CHP(3.0) | E11(42) | E32(20) | — | BHT(0.1) | — |
| Example B7 | First paste | DEPT(1.0) | E12(10) | E32(300) | — | BHT(0.1) | — |
| | Second paste | BPO(1.5) | E12(10) | E32(300) | — | BHT(0.1) | — |
| Example B8 | First paste | PTU(1), VOA(0.1) | E12(15) | E33(300) | — | BHT(0.1) | FA(0.05) |
| | Second paste | CHP(3.0) | E12(15) | E33(300) | — | BHT(0.1) | — |
| Example B9 | First paste | PTU(1.0), COA(0.01) | E15(15) | E31(250) | E34(15) | BHT(0.1) | FA(0.01) |
| | Second paste | TMBH(2) | E15(15) | E31(250) | E34(15) | BHT(0.1) | — |
| Example B10 | First paste | PTU(1.0), COA(0.01) | E12(15) | E31(200) | — | BHT(0.1) | FA(0.05) |
| | Second paste | CHP(0.5) | E12(15) | E31(200) | — | BHT(0.1) | — |
| Example B11 | First paste | PTU(1.0), COA(0.01) | E12(15) | E33(200) | — | BHT(0.1) | FA(0.01) |
| | Second paste | CHP(0.5) | E12(15) | E33(200) | — | BHT(0.1) | — |
| Example B12 | First paste | BTU(1), VOA(0.001) | E15(15) | E31(200) | — | BHT(0.1) | FA(0.05) |
| | Second paste | CHP(2) | E15(15) | E31(200) | — | BHT(0.1) | — |
| Example B13 | First paste | DEPT(1.0) | E14(15) | E32(200) | — | BHT(0.1) | FA(0.05) |
| | Second paste | BPO(1.5) | E14(15) | E32(200) | — | BHT(0.1) | — |
| Example B14 | First paste | VOA(0.1), COA(0.01) | E11(15) | E33(200) | — | BHT(0.1) | FA(0.05) |
| | Second paste | BPO(1.0), TPE(1.0) | E11(15) | E33(200) | — | BHT(0.1) | — |
| Example B15 | First paste | BTU(2.0), VOA(0.005) | E15(15) | E32(200) | — | BHT(0.1) | FA(0.05) |
| | Second paste | CHP(3.0) | E15(15) | E32(200) | — | BHT(0.1) | — |
| Example B16 | First paste | PTU(2.0) | E15(15) | E31(200) | — | BHT(0.1) | — |
| | Second paste | CHP(3.0) | E15(15) | E31(200) | — | BHT(0.1) | — |
| Example B17 | First paste | PTU(2.0), VOA(0.005) | E14(15) | E32(200) | — | BHT(0.1) | — |
| | Second paste | CHP(3.0) | E14(15) | E32(200) | — | BHT(0.1) | — |
| Example B18 | First paste | BTU(1.5), VOA(0.005) | E15(15) | E32(200) | — | BHT(0.1) | — |
| | Second paste | CHP(2.0) | E15(15) | E32(200) | — | BHT(0.1) | — |
| Example B19 | First paste | PTU(1.5), VOA(0.005) | E11(15) | E32(200) | — | BHT(0.1) | — |
| | Second paste | CHP(2.0) | E11(15) | E32(200) | — | BHT(0.1) | — |
| Example B20 | First paste | PTU(1.5), VOA(0.005) | E21(15) | E31(250) | — | BHT(0.1) | FA(0.05) |
| | Second paste | CHP(2.0) | E21(15) | E31(250) | — | BHT(0.1) | — |
| Example B21 | First paste | PTU(1.5), VOA(0.005) | E22(20) | E33(250) | — | BHT(0.1) | FA(0.05) |
| | Second paste | CHP(2.0) | E22(20) | E33(250) | — | BHT(0.1) | — |
| Example B22 | First paste | CHP(2.0) | E12(15) | E32(200) | — | BHT(0.1) | FA(0.05) |
| | Second paste | PTU(1.5), VOA(0.005) | E12(15) | E32(200) | — | BHT(0.1) | — |
| Example B23 | First paste | PTU(1.6), COA(0.01) | E12(15) | E32(200) | — | BHT(0.1) | FA(0.01) |
| | Second paste | CHP(1.8) | E12(15) | E32(200) | — | BHT(0.1) | BT(1) |
| Comparative Example CB1 | First paste | PTU(1.6), COA(0.01) | — | E32(200) | — | BHT(0.1) | — |
| | Second paste | CHP(1.8) | — | E32(200) | — | BHT(0.1) | — |
| Comparative Example CB2 | First paste | PTU(1.0), COA(0.01) | E12(15) | E33(200) | — | BHT(0.1) | — |
| | Second paste | CHP(1.5) | E12(15) | E33(200) | — | BHT(0.1) | — |
| Comparative Example CB3 | First paste | PTU(1.0), COA(0.01) | E12(15) | E33(200) | — | BHT(0.1) | — |
| | Second paste | CHP(1.5) | E12(15) | E33(200) | — | BHT(0.1) | — |
| Comparative Example CB4 | First paste | VOA(0.1), COA(0.01) | E12(15) | E33(200) | — | BHT(0.1) | — |
| | Second paste | BPO(1.0), TPE(1.0) | E12(15) | E33(200) | — | BHT(0.1) | — |

The test methods adopted in Examples and Comparative Examples are as follows. For one pack type dental photocurable composition, the dental photocurable composition was used by dispensing from a syringe container. For two packs type dental photocurable composition, a paste prepared by mixing the pastes 1 and 2 using a mixing tip manufactured by Mixpack Co., Ltd. was used. When using, a paste prepared by mixing the pastes 1 and 2 with a mixing chip manufactured by Mixpack Co., Ltd. was used. The mixing chip manufactured by Mixpack Co., Ltd. can perform mixing by a static mixer, and when using it, the pastes 1 and 2 can be kneaded at a volume ratio of 0.9 to 1.1:2, ideally at equal volumes. The paste 1 and paste 2 were kneaded so as to have a mass ratio of 0.8 to 1.2:1.0 and used.

(1) Flexural Strength

The prepared dental photocurable composition was filled into a stainless steel mold, and the cover glasses were placed on both sides to press with a glass kneading plate. Thereafter, light was irradiated for 10 seconds to 5 locations by using the photopolymerization irradiator (Blue Shot manufactured by SHOFU INC.) to cure the composition. After curing, the cured product was removed from the mold, and light was irradiated to the backside in the same manner again to use as a test specimen (25×2×2 mm rectangular shape).

For one pack type dental photocurable composition, the test specimen was immersed in water at 37° C. for 24 hours, and thereafter flexural test was performed. For two packs type dental photocurable composition, flexural test was performed within 1 hour after irradiating the test specimen with light. The flexural test was conducted at a distance between supporting points of 20 mm and at a crosshead speed of 1 mm/min using an Instron universal testing machine (manufactured by Instron).

In the case of containing 150 parts by mass or more of the (E) filler with respect to 100 parts by mass of the (A) polymerizable monomer, evaluation criteria for flexural strength of the one pack type dental photocurable composition and the two packs type dental photocurable composition were as follows.
Good: more than 100 MPa
Applicable: 80 MPa or more and 100 MPa or less
Insufficient: less than 80 MPa In the case of containing less than 150 parts by mass of the (E) filler with respect to 100 parts by mass of the (A) polymerizable monomer, evaluation criteria for flexural strength of the one pack type dental photocurable composition and the two packs type dental photocurable composition were as follows.
Good: more than 80 MPa
Applicable: 60 MPa or more and 80 MPa or less
Insufficient: less than 60 MPa Since the flexural strength differs depending on the compounding amount of the filler, different criteria were set.

(2) Fluidity

For an initial preparation product of a dental photocurable composition and an acceleration test product prepared by standing in a thermostatic chamber set at 50° C. for one month, the distance moved by the dental photocurable composition in 1 minute after vertically fixing a glass slide so as to make an angle at 90° to the horizontal plane in 5 seconds after adhering 0.05 g of the dental photocurable composition in a lump state on the horizontally placed slide glass plane was measured. This movement distance (unit: mm) was defined as fluidity. When the fluidity was 20 mm or more, it was determined that the expected rheological property was not exhibited. Evaluation criteria were as follows.

Particularly good storage stability: the change between the initial preparation product and the acceleration test product was less than 1 mm.
Good storage stability: the change between the initial preparation product and the acceleration test product was 1 mm or more and less than 2 mm.
Usable storage stability: the change between the initial preparation product and the acceleration test product was 2 mm or more and 3 mm or less.

On the other hand, when the change of the fluidity was more than 3 mm, because there was a high possibility that the operability changed after long-term storage, it was evaluated as insufficient storage stability.

(3) Color Stability after Irradiation

Each prepared dental photocurable composition was filled into a mold (in a shape of a disc having a diameter of 15 mm and a thickness of 1 mm) made of stainless steel. Thereafter, a cover glass was placed on upper side of the stainless mold to apply pressure with glass plate. Subsequently, light irradiation was performed for 1 minute using a photopolymerization irradiator (Grip Light II, manufactured by SHOFU Inc.) via the cover glass to prepare a cured product. The cured product was taken out of the mold, the cover glass was removed and the test specimen was measured for color tone.

Color measurement was performed by placing the test specimen on the background of a standard white plate (D65/10°, X=81.07, Y=86.15, Z=93.38) and using a spectrocolorimeter (manufactured by BYK-Chemie GmbH) under predetermined condition (light source: C, viewing angle: 2°, measurement area: 11 mm). Then, after exposing the test specimen to light for 24 hours with a xenon lamp light exposure tester (Suntest CPS+), the color tone of the test specimen was measured again, and the difference in discoloration was represented by ΔE calculated from the following formula.

$$\Delta E = ((\Delta L^*)^2 + (\Delta a^*)^2 + (\Delta b^*)^2)/2$$

$$\Delta L^* = L1^* - L2^*$$

$$\Delta a^* = a1^* - a2^*$$

$$\Delta b^* = b1^* - b2^*$$

In the formula, L1* is the brightness index before light exposure, L2* is the brightness index after light exposure, a1* and b1* are the color quality index before light exposure, and a2* and b2* are the color quality index after light exposure. Evaluation criteria were as follows.
A (Particularly good): ΔE was less than 5
B (Good): ΔE was 5 or more and less than 8
C (Usable): ΔE was 8 or more and 10 or less
D (Insufficient): ΔE was more than 10

The color stability after irradiation was measured for predict the color tone change when the cured product was used for a long period of time in the light exposed area, and the smaller ΔE, the smaller the color change when the cured product was exposed with light for a long period of time.

The results shown in Tables 5 to 6 will be described.

TABLE 5

| One pack type dental photocurable composition | Flexural strength (MPa) | Fluidity Initial preparation Measured value (mm) | Acceleration test Measured value (mm) | Change amount (mm) | Color stability after irradiation |
|---|---|---|---|---|---|
| Example A1 | 104 | 17.0 | 19.5 | 2.5 | A |
| Example A2 | 110 | 13.0 | 14.5 | 1.5 | A |
| Example A3 | 111 | 8.0 | 8.0 | 0.0 | A |
| Example A4 | 105 | 0.0 | 0.0 | 0.0 | A |
| Example A5 | 115 | 0.0 | 0.0 | 0.0 | A |
| Example A6 | 90 | 0.0 | 0.0 | 0.0 | A |
| Example A7 | 124 | 0.0 | 0.0 | 0.0 | A |
| Example A8 | 81 | 2.0 | 2.0 | 0.0 | C |
| Example A9 | 110 | 1.0 | 1.0 | 0.0 | B |
| Example A10 | 81 | 1.0 | 1.0 | 0.0 | C |
| Example A11 | 83 | 1.0 | 1.0 | 0.0 | C |
| Example A12 | 81 | 1.5 | 1.5 | 0.0 | B |
| Example A13 | 122 | 1.0 | 1.0 | 0.0 | C |
| Example A14 | 101 | 1.5 | 1.5 | 0.0 | B |
| Example A15 | 103 | 2.0 | 2.0 | 0.0 | C |
| Example A16 | 105 | 1.0 | 1.0 | 0.0 | C |
| Example A17 | 104 | 1.0 | 1.0 | 0.0 | C |
| Example A18 | 105 | 2.0 | 2.0 | 0.0 | C |
| Example A19 | 101 | 1.0 | 1.0 | 0.0 | C |
| Example A20 | 105 | 1.0 | 1.0 | 0.0 | C |
| Example A21 | 81 | 1.5 | 1.5 | 0.0 | A |
| Example A22 | 109 | 0.0 | 0.0 | 0.0 | C |
| Example A23 | 81 | 0.0 | 0.0 | 0.0 | A |
| Example A24 | 92 | 0.0 | 0.0 | 0.0 | A |
| Example A25 | 85 | 0.0 | 0.0 | 0.0 | A |
| Example A26 | 93 | 0.0 | 0.0 | 0.0 | A |
| Example A27 | 108 | 2.0 | 4.0 | 2.0 | A |
| Example A28 | 114 | 2.0 | 4.5 | 2.5 | A |

TABLE 5-continued

| One pack type dental photocurable composition | Flexural strength (MPa) | Fluidity | | | Color stability after irradiation |
|---|---|---|---|---|---|
| | | Initial preparation Measured value (mm) | Acceleration test Measured value (mm) | Change amount (mm) | |
| Example A29 | 122 | 1.0 | 3.5 | 2.5 | A |
| Example A30 | 118 | 2.0 | 4.0 | 2.0 | A |
| Example A31 | 124 | 1.5 | 3.0 | 1.5 | A |
| Example A32 | 125 | 1.5 | 3.0 | 1.5 | A |
| Example A33 | 116 | 1.0 | 2.0 | 1.0 | A |
| Example A34 | 113 | 8.0 | 8.5 | 0.5 | A |
| Example A35 | 123 | 8.5 | 8.5 | 0.0 | A |
| Example A36 | 114 | 1.5 | 2.0 | 0.5 | C |
| Example A37 | 110 | 1.0 | 1.5 | 0.5 | A |
| Example A38 | 122 | 1.0 | 1.0 | 0.0 | A |
| Comparative Example CA1 | Uncured | 1.0 | 1.5 | 0.5 | A |
| Comparative Example CA2 | 62 | 1.5 | 1.5 | 0.0 | A |
| Comparative Example CA3 | 104 | 25.0 | 27.0 | 2.0 | A |
| Comparative Example CA4 | 101 | 1.0 | 3.5 | 2.5 | A |
| Comparative Example CA5 | 106 | 1.0 | 7.0 | 6.0 | A |
| Comparative Example CA6 | 101 | 1.0 | 10.0 | 9.0 | A |

TABLE 6

| Two packs type dental photocurable composition | Flexural strength (MPa) | Fluidity | | | Color stability after irradiation |
|---|---|---|---|---|---|
| | | Initial preparation Measured value (mm) | Acceleration test Measured value (mm) | Change amount (mm) | |
| Example B1 | 106 | 17.0 | 19.5 | 2.5 | A |
| Example B2 | 101 | 13.0 | 14.5 | 1.5 | A |
| Example B3 | 118 | 8.0 | 8.0 | 0.0 | A |
| Example B4 | 118 | 0.0 | 0.0 | 0.0 | A |
| Example B5 | 123 | 0.0 | 0.0 | 0.0 | A |
| Example B6 | 91 | 0.0 | 0.0 | 0.0 | A |
| Example B7 | 126 | 0.0 | 0.0 | 0.0 | A |
| Example B8 | 92 | 2.0 | 2.0 | 0.0 | C |
| Example B9 | 82 | 1.0 | 1.0 | 0.0 | C |
| Example B10 | 83 | 1.5 | 1.5 | 0.0 | B |
| Example B11 | 106 | 1.5 | 1.5 | 0.0 | B |
| Example B12 | 107 | 2.0 | 2.0 | 0.0 | C |
| Example B13 | 80 | 1.5 | 1.5 | 0.0 | A |
| Example B14 | 122 | 0.0 | 0.0 | 0.0 | C |
| Example B15 | 113 | 2.0 | 4.0 | 2.0 | A |
| Example B16 | 110 | 2.0 | 4.5 | 2.5 | A |
| Example B17 | 107 | 1.0 | 3.5 | 2.5 | A |
| Example B18 | 125 | 1.5 | 3.0 | 1.5 | A |
| Example B19 | 115 | 1.0 | 2.0 | 1.0 | A |
| Example B20 | 120 | 8.0 | 8.5 | 0.5 | A |
| Example B21 | 112 | 8.5 | 8.5 | 0.0 | A |
| Example B22 | 106 | 1.5 | 2.0 | 0.5 | C |
| Example B23 | 122 | 1.0 | 1.5 | 0.5 | A |
| Comparative Example CB1 | 108 | 31.0 | 33.0 | 2.0 | A |
| Comparative Example CB2 | 69 | 1.0 | 6.0 | 5.0 | A |
| Comparative Example CB3 | 82 | 1.0 | 7.0 | 6.0 | A |
| Comparative Example CB4 | 111 | 1.0 | 10.0 | 9.0 | A |

It was confirmed that the compositions described in Examples had sufficient flexural strength, excellent operability and storage stability.

When the compounding amount of the (E1) hydrophobized silica fine particle having an average diameter of primary particle of 1 to 40 nm was less than 1 part by mass as Examples A1, A2, B1, and B2, there was a tendency that fluidity was high. When the compounding amount of the (E1) hydrophobized silica fine particle having an average diameter of primary particle of 1 to 40 nm was more than 20 parts by mass as Examples A5, A6, B5, and B6, although there was no problem in the physical property and the storage stability, there was a tendency that the paste was thickened, the feeling in extruding became heavy, and the operability deteriorate. This was particularly remarkable in Examples A6 and B6 in which the compounding amount of the (E1) hydrophobized silica fine particle having an average diameter of primary particle of 1 to 40 nm exceeded 30 parts by mass.

When the total amount of the (E1) hydrophobized silica fine particle having an average diameter of primary particle of 1 to 40 nm and the (E2) inorganic filler having an average diameter of primary particle of 0.1 to 10 μm, with respect to 100 parts by mass of the (A) polymerizable monomer, was less than 100 parts by weight as Examples A23 to A26, there was a tendency that flexural strength decreased. On the other hand, when the total amount of the (E1) hydrophobized silica fine particle having an average diameter of primary particle of 1 to 40 nm and the (E2) inorganic filler having an average diameter of primary particle of 0.1 to 10 μm, with respect to 100 parts by mass of the (A) polymerizable monomer, exceeded 400 parts by weight as Example A7, there was a tendency that the paste was thickened, the feeling in extruding became heavy, and the operability deteriorate.

In Examples A34, A35, B20 and B21 containing fine particles E21 and E22 which were hydrophobized by surface treatment with a silane coupling agent having a polymerizable group among the (E1) hydrophobized silica fine particle having an average diameter of primary particle of 1 to 40 nm, thixotropic property with respect to the compounding amount was weaker than fine particles surface-treated with dimethyl silicone oil or functional groups such as trimethylsilyl group, dimethylsilyl group, methylsilyl group and alkylsilyl group, a slightly high value of the fluidity showed.

In the composition containing an amine compound having one substituent consisting of three or more carbons having an electron-withdrawing group at α-carbon and/or β-carbon of the amine starting from N as Examples A27 to A30 and B15 to B17, although the amount of change in the fluidity was within an acceptable range, there was a tendency that the amount of change in fluidity after storage at 50° C. for 1 month increased. In addition, in the composition containing an amine compound having two substituents consisting of three or more carbons having an electron-withdrawing group at α-carbon and/or β-carbon of the amine starting from N as Examples A31 to A33, B18 and B19, there was a tendency that amount of change in the fluidity after storage at 50° C. for 1 month was slightly large.

In the composition containing an aromatic amine compound in addition to the (D1) aliphatic tertiary amine compound represented by formula (1) as Examples A36 and B22, there was a tendency that the change in fluidity was small, but the color stability after irradiation was poor. On the other hand, in the composition containing an aromatic amine compound as in Examples A37 and B23, there was a tendency that the decrease in color stability after irradiation was suppressed by adding an ultraviolet absorber.

In the composition in which the compounding amount of the (B) photosensitizer is less than 0.02 parts by mass with respect to the (A) polymerizable monomer as Examples A8 and B8, there was a tendency that the flexural strength was slightly inferior. In Examples A10, A11 and B9 not containing the (C) photoacid generator, there was a tendency that the flexural strength and the color stability after irradiation were slightly inferior. In Examples A21 and B13 in which the compounding amount of the (D) photopolymerization accelerator was small, there was a tendency that flexural strength was slightly inferior.

In Examples A9, A10, A12 and B7 in which the compounding amount of the photosensitizer was large, there was a tendency that the color stability after irradiation was slightly inferior. In the case that the compounding amount of the (C) photoacid generator, with respect to 100 parts by mass of the (A) polymerizable monomer, was as large as 10 parts by mass or more as Examples A8, A13 and B8, there was a tendency that the color stability after irradiation was slightly inferior. In the case that the compounding amount of the (C) photoacid generator was as small as 0.1 parts by mass or less as Examples A12 and B10, there was a tendency that flexural strength was slightly inferior. Furthermore, in the composition containing an aryliodonium salt compound of an anion having no organic chain as the photoacid generator as Examples A15 to A20 and B12 and in the composition containing a triazine compound as the photoacid generator as Examples A14 and 1311, there was a tendency that the color stability after irradiation was slightly inferior. In Examples A22 and B14 in which the compounding amount of the (D) photopolymerization accelerator was large, there was a tendency that the color stability after irradiation was slightly inferior.

Because Comparative Examples CA1 did not contain the (B) photosensitizer, this was not cured. Since Comparative Examples CA2 did not contain the (D) photopolymerization accelerator, the flexural strength was remarkably low. Since Comparative Examples CA3 and CB1 did not contain the (E1) hydrophobized silica fine particle having an average diameter of primary particle of 1 to 40 nm, the fluidity was large and thixotropy property was not exhibited. Since Comparative Examples CA4 to CA6 and CB2 to CB4 contained the (D) photopolymerization accelerator other than the (D1) aliphatic tertiary amine compound represented by formula (1), the amount of change in fluidity after storage at 50° C. for one month was large, and the rheological property was deactivated.

The dental photocurable composition of the present disclosure evaluated in Examples can be used for any known dental photocurable composition without any problem. The dental photocurable composition includes a dental adhesive material, a dental primer, a dental composite resin, a dental core build-up material, a dental resin cement, a dental coating material, a dental sealant material, a dental manicure material, a dental room temperature polymerization resin, a dental splinting material, a dental glass ionomer cement, a dental hard resin, a dental CAD-CAM restoration material, a dental 3D printer material and the like.

With respect to the use of substantially any plural and/or singular terms herein, those having skill in the art can translate from the plural to the singular and/or from the singular to the plural as is appropriate to the context.

Although the description herein has been given with reference to the drawings and embodiments, it should be noted that those skilled in the art may make various changes and modifications on the basis of this disclosure without difficulty. Accordingly, any such changes and modifications are intended to be included in the scope disclosure the embodiments.

INDUSTRIAL APPLICABILITY

The present disclosure may provide a dental photocurable composition which has sufficient mechanical property and whose rheological property is not deactivated even after long-term storage.

What is claimed is:
1. A dental photocurable composition, comprising (A) polymerizable monomer, (B) photosensitizer, (D) photopolymerization accelerator and (E) filler, wherein,
the (A) polymerizable monomer has a (meth) acrylic group and/or a (meth) acrylamide group as the polymerizable group,
the (B) photosensitizer comprises α-diketones,
the dental photocurable composition comprises (D1) aliphatic tertiary amine compound represented by formula (1) as the (D) photopolymerization accelerator,
the dental photocurable composition comprises (E1) hydrophobized silica fine particle having an average diameter of primary particle of 1 to 40 nm as the (E) filler,
the (E1) hydrophobized silica fine particle is a hydrophobic silica fine particle hydrophobized by surface treatment with a silane coupling agent and/or a modified silicone oil, and
the dental photocurable composition comprises, with respect to 100 parts by mass of the (A) polymerizable monomer,
0.02 to 1 parts by mass of the (B) photosensitizer,
0.1 to 10 parts by mass of the (D1) aliphatic tertiary amine compound, and
0.5 to 30 parts by mass of the (E1) hydrophobized silica fine particle,

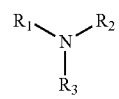

[Formula 1]

wherein $R_1$ represents a substituent consisting of three or more carbons having an electron-withdrawing group at α-carbon and/or β-carbon of an amine starting from N, $R_2$ represents a substituent consisting of three or more carbons which may have an electron-withdrawing group, $R_3$ represents a substituent consisting of one or more carbons which may have an electron-withdrawing group, and a-carbon of N in the formula (1) is not an electron-withdrawing group, and
wherein the electron-withdrawing group of $R_1$ is a substituent selected from a functional group selected from the group consisting of a hydroxyl group, a carboxyl group, a vinyl group, an aryl group and a halogen, and, an organic group which is bonded via an ether bond, an ester bond, a urethane bond or a urea bond and may have —OH group, —O-group, —C(O)-group, —S-group, —NH—C(O)—NH-group, —C(O)—O-group, —O—C(O)-group, —OC(O)—NH-group, —NH—C(O)—O-group, an aromatic hydrocarbon group, or a polymerizable functional group capable of radical polymerization.

2. The dental photocurable composition according to claim 1, wherein
the (D1) aliphatic tertiary amine compound represented by formula (1) is an aliphatic tertiary amine compound in which $R_1$ and $R_2$ have an aliphatic substituent consisting of three or more carbons having an electron-withdrawing group at α-carbon and/or β-carbon.

3. The dental photocurable composition according to claim 1, wherein
the (D1) aliphatic tertiary amine compound represented by formula (1) is an aliphatic tertiary amine compound in which $R_1$ and $R_2$ have an aryl group at α-carbon and/or β-carbon.

4. The dental photocurable composition according to claim 1, wherein
the (E1) hydrophobized silica fine particle having an average diameter of primary particle of 1 to 40 nm is hydrophobized by surface treatment with dimethyl silicone oil or by surface treatment by covalent bonding of a functional group selected from the group consisting of trimethylsilyl group, dimethylsilyl group, methylsilyl group, and alkylsilyl group having a linear alkyl chain in which the carbon atom number is between 3 and 18, to the fine particle.

5. The dental photocurable composition according to claim 1, wherein
the dental photocurable composition further comprises (E2) inorganic filler having an average diameter of primary particle of 0.1 to 10 μm as the (E) filler, and
a total amount of the (E2) inorganic filler and the (E1) hydrophobized silica fine particle is 100 to 400 parts by mass with respect to 100 parts by mass of the (A) polymerizable monomer.

6. The dental photocurable composition according to claim 1, wherein
the dental photocurable composition further comprises an aryl iodonium salt as a (C) photoacid generator, and
the aryl iodonium salt is a salt of an anion having an organic group and one or more atoms selected from the group consisting of P, B, Al, S and Ga, and an aryl iodonium cation.

7. The dental photocurable composition according to claim 1, wherein
the dental photocurable composition further comprises an aryl iodonium salt as a (C) photoacid generator, and
the aryl iodonium salt is a salt of an anion having an organic group in which at least one H is substituted with F and one or more atoms selected from the group consisting of P, B, Al, S and Ga, and an aryl iodonium cation.

8. The dental photocurable composition according to claim 1, wherein
the dental photocurable composition is one pack type dental photocurable composition comprising,
with respect to 100 parts by mass of the (A) polymerizable monomer,
0.02 to 1 parts by mass of the (B) photosensitizer,
0.1 to 10 parts by mass of the (D1) aliphatic tertiary amine compound,
0.5 to 30 parts by mass of the (E1) hydrophobized silica fine particle having an average diameter of primary particle of 1 to 40 nm.

9. The dental photocurable composition according to claim 6, wherein
the dental photocurable composition is one pack type dental photocurable composition comprising,
with respect to 100 parts by mass of the (A) polymerizable monomer,
0.02 to 1 parts by mass of the (B) photosensitizer,
0.1 to 10 parts by mass of the (C) photoacid generator,
0.1 to 10 parts by mass of the (D1) aliphatic tertiary amine compound,
0.5 to 30 parts by mass of the (E1) hydrophobized silica fine particle having an average diameter of primary particle of 1 to 40 nm.

10. The dental photocurable composition according to claim 1, wherein
the dental photocurable composition is two packs type dental photocurable composition consisting of a first paste and a second paste,
a mass ratio of the first paste and the second paste is 1:0.8 to 1.2,
both the first paste and the second paste comprise the (E1) hydrophobized silica fine particle having an average diameter of primary particle of 1 to 40 nm,
the dental photocurable composition comprises, with respect to 200 parts by mass of total of the (A) polymerizable monomer contained in the first paste and the second paste,
0.04 to 2 parts by mass of the (B) photosensitizer,
0.2 to 20 parts by mass of the (D1) aliphatic tertiary amine compound,
1 to 60 parts by mass of the (E1) hydrophobized silica fine particle having an average diameter of primary particle of 1 to 40 nm.

11. The dental photocurable composition according to claim 6, wherein
the dental photocurable composition is two packs type dental photocurable composition consisting of a first paste and a second paste,
a mass ratio of the first paste and the second paste is 1:0.8 to 1.2,
both the first paste and the second paste comprise the (E1) hydrophobized silica fine particle having an average diameter of primary particle of 1 to 40 nm,
the dental photocurable composition comprises, with respect to 200 parts by mass of total of the (A) polymerizable monomer contained in the first paste and the second paste,
0.04 to 2 parts by mass of the (B) photosensitizer,
0.2 to 20 parts by mass of the (C) photoacid generator,
0.2 to 20 parts by mass of the (D1) aliphatic tertiary amine compound,
1 to 60 parts by mass of the (E1) hydrophobized silica fine particle having an average diameter of primary particle of 1 to 40 nm.

12. The dental photocurable composition according to claim 1, wherein
the difference between a flowability of the dental photocurable composition after standing in a thermostatic chamber set at 50° C. for one month after preparation and a flowability of the dental photocurable composition after preparation is 3.0 mm or less.

13. The dental photocurable composition according to claim 1, wherein
both the flowability of the dental photocurable composition after standing in a thermostatic chamber set at 50° C. for one month after preparation and the flowability of the dental photocurable composition after preparation are 3.0 mm or less.

* * * * *